US012349866B2

(12) United States Patent  
Sørensen et al.

(10) Patent No.: US 12,349,866 B2  
(45) Date of Patent: Jul. 8, 2025

(54) TIP PART FOR AN ENDOSCOPE

(71) Applicant: AMBU A/S, Ballerup (DK)

(72) Inventors: Morten Sørensen, Ballerup (DK); Lasse Markworth Johnsen, Birkerød (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 18/240,503

(22) Filed: Aug. 31, 2023

(65) Prior Publication Data

US 2023/0414072 A1    Dec. 28, 2023

Related U.S. Application Data

(63) Continuation of application No. 17/157,769, filed on Jan. 25, 2021, now Pat. No. 11,786,108.

(30) Foreign Application Priority Data

Jan. 28, 2020   (EP) .................................... 20153967

(51) Int. Cl.  
*A61B 1/00* (2006.01)  
*A61B 1/005* (2006.01)  
(Continued)

(52) U.S. Cl.  
CPC ........ *A61B 1/0011* (2013.01); *A61B 1/00066* (2013.01); *A61B 1/00091* (2013.01); *A61B 1/00096* (2013.01); *A61B 1/009* (2022.02); *A61B 1/015* (2013.01); *A61B 1/018* (2013.01); *A61B 1/051* (2013.01); *A61B 1/0661* (2013.01);  
(Continued)

(58) Field of Classification Search  
None  
See application file for complete search history.

(56) References Cited

U.S. PATENT DOCUMENTS

| 5,419,311 A | * | 5/1995 | Yabe ..................... A61B 1/015 600/124 |
| 5,499,625 A | | 3/1996 | Frass et al. |

(Continued)

FOREIGN PATENT DOCUMENTS

| DE | 3004089 A1 | 8/1980 |
| EP | 0161834 A1 | 11/1985 |

(Continued)

OTHER PUBLICATIONS

Examination Report issued for EP Patent Application No. 20153967. 3, dated Jan. 24, 2024, 5 pages.

(Continued)

*Primary Examiner* — Michael J Carey  
*Assistant Examiner* — Jae Woo  
(74) *Attorney, Agent, or Firm* — Faegre Drinker Biddle & Reath LLP

(57) ABSTRACT

A disposable endoscope with a tip part including a vision sensor, an exterior housing having a front wall and a circumferential wall, an interior spacing of the exterior housing accommodating the vision sensor, and a camera window positioned at least partly in front of the vision sensor, the housing further comprising a nozzle provided at the distal end of the tip part and configured to flush an exterior surface of the window, wherein the front wall and the nozzle are integrally formed in one piece from one polymer material.

21 Claims, 8 Drawing Sheets

(51) Int. Cl.
  *A61B 1/015* (2006.01)
  *A61B 1/018* (2006.01)
  *A61B 1/05* (2006.01)
  *A61B 1/06* (2006.01)
  *A61B 1/07* (2006.01)
  *A61B 1/12* (2006.01)

(52) U.S. Cl.
  CPC ............... *A61B 1/07* (2013.01); *A61B 1/126* (2013.01); *A61B 1/00097* (2022.02); *A61B 1/05* (2013.01)

(56) References Cited

U.S. PATENT DOCUMENTS

| | | | |
|---|---|---|---|
| 5,536,236 A | 7/1996 | Yabe et al. | |
| 5,562,602 A | 10/1996 | Yabe et al. | |
| 5,575,756 A * | 11/1996 | Karasawa | A61B 1/0014 600/156 |
| 5,685,823 A | 11/1997 | Ito et al. | |
| 5,688,221 A * | 11/1997 | Yabe | A61B 1/042 600/139 |
| 5,725,476 A | 3/1998 | Yasui et al. | |
| 5,788,628 A | 8/1998 | Matsuno et al. | |
| 6,248,060 B1 | 6/2001 | Buess et al. | |
| 6,409,657 B1 * | 6/2002 | Kawano | A61B 1/125 600/157 |
| 6,447,445 B1 | 9/2002 | Hirano | |
| 6,569,089 B1 * | 5/2003 | Covington | A61B 1/267 600/199 |
| 7,630,148 B1 * | 12/2009 | Yang | G02B 23/243 359/740 |
| 8,485,966 B2 | 7/2013 | Robertson | |
| 10,245,402 B2 | 4/2019 | Daher et al. | |
| 10,321,804 B2 | 6/2019 | Jacobsen et al. | |
| 10,406,309 B2 | 9/2019 | Daher | |
| 11,291,352 B2 | 4/2022 | Vilhelmsen et al. | |
| 11,786,108 B2 | 10/2023 | Sørensen et al. | |
| 2007/0249907 A1 | 10/2007 | Boulais et al. | |
| 2008/0188715 A1 * | 8/2008 | Fujimoto | A61B 1/126 600/157 |
| 2008/0200764 A1 * | 8/2008 | Okada | A61B 1/00068 600/157 |
| 2009/0227998 A1 | 9/2009 | Aljuri et al. | |
| 2009/0247831 A1 * | 10/2009 | Miyamoto | A61B 1/00091 600/157 |
| 2009/0253964 A1 * | 10/2009 | Miyamoto | G02B 23/2476 600/157 |
| 2012/0041534 A1 | 2/2012 | Clerc et al. | |
| 2012/0172664 A1 | 7/2012 | Hayman et al. | |
| 2012/0259173 A1 | 10/2012 | Waldron et al. | |
| 2013/0131453 A1 * | 5/2013 | Imai | A61B 1/00091 600/156 |
| 2014/0150782 A1 * | 6/2014 | Vazales | A61M 25/1018 128/202.16 |
| 2015/0257633 A1 | 9/2015 | Hassidov et al. | |
| 2015/0272430 A1 * | 10/2015 | Oishi | A61B 1/0011 600/112 |
| 2017/0072193 A1 * | 3/2017 | Heller | A61N 1/0502 |
| 2017/0245734 A1 | 8/2017 | Kaneko | |
| 2018/0078120 A1 * | 3/2018 | Poll | A61B 1/2736 |
| 2018/0160886 A1 | 6/2018 | Govani et al. | |
| 2018/0325359 A1 * | 11/2018 | Watanabe | G02B 23/2476 |
| 2019/0282070 A1 * | 9/2019 | Vilhelmsen | B29C 45/16 |
| 2019/0282077 A1 * | 9/2019 | Sørensen | A61B 1/0011 |
| 2019/0313891 A1 | 10/2019 | Oka | |
| 2021/0228064 A1 * | 7/2021 | Sørensen | A61B 1/00066 |
| 2023/0054149 A1 | 2/2023 | Sørensen et al. | |
| 2023/0068676 A1 | 3/2023 | Sørensen et al. | |
| 2024/0090745 A1 * | 3/2024 | Schroeter | A61B 1/126 |

FOREIGN PATENT DOCUMENTS

| | | |
|---|---|---|
| EP | 0497347 A2 | 8/1992 |
| EP | 0587177 A1 | 3/1994 |
| EP | 1759625 A1 | 3/2007 |
| EP | 2106739 A2 | 10/2009 |
| EP | 3539449 A1 | 9/2019 |
| JP | 08-286127 A | 11/1996 |
| JP | 11-188004 A | 7/1999 |
| JP | 5566344 B2 | 8/2014 |
| WO | 94/22358 A1 | 10/1994 |
| WO | 2010/066790 A1 | 6/2010 |

OTHER PUBLICATIONS

European Search Report for EP Patent Application No. 20153967.3, Issued on Aug. 7, 2020, 8 pages.
International Search Report and Written Opinion of International Application No. PCT/EP2020/083525, dated Apr. 1, 2021, 16 pages.
International Search Report and Written Opinion of International Application No. PCT/EP2020/083527, dated Jan. 19, 2021, 10 pages.

\* cited by examiner

TIP PART FOR AN ENDOSCOPE

CROSS-REFERENCE TO RELATED APPLICATIONS

This application is a continuation of U.S. patent application Ser. No. 17/157,769, filed Jan. 25, 2021, which claims priority to and the benefit of European Patent Application No. EP20153967, filed Jan. 28, 2020, all said applications are incorporated herein by reference in their entirety.

TECHNICAL FIELD

The present disclosure relates to insertable medical vision devices, such as, but not limited to, endotracheal tubes and endoscopes, in particular disposable insertion endoscopes, more specifically to a tip part of such a vision device, to an endoscope with such a tip part, and to a method of manufacture of such a tip part, the tip part comprising a nozzle.

BACKGROUND

Vision devices, such as endoscopes, are well known for visually inspecting inaccessible places such as human body cavities. Typically, the endoscope comprises an elongated insertion tube with a handle at the proximal end, as seen from the operator, and visual inspection means, such as a built-in camera including a vision sensor, at a distal end of the elongated insertion tube. This definition of the terms distal and proximal, i.e. "proximal" being the end closest to the operator and "distal" being the end remote from the operator, as used herein for endoscopes in general, is adhered to in the present specification. Electrical wiring for the camera and other electronics, such as one or more LEDs accommodated in the tip part at the distal end, runs along the inside of the elongated insertion tube from the handle to the tip part. A working or suction channel may run along the inside of the insertion tube from the handle to the tip part, e.g. allowing liquid to be removed from the body cavity or allowing for insertion of surgical instruments or the like into the body cavity. The suction channel may be connected to a suction connector, typically positioned at a handle at the proximal end of the insertion tube.

To be able to maneuver the endoscope inside the body cavity, the distal end of the endoscope may comprise a bending section with increased flexibility, e.g. a number of articulated segments of which the tip part or an external housing thereof may form the distalmost segment. The maneuvering of the endoscope inside the body is typically done by tensioning or slacking pull wires also running along the inside of the elongated insertion tube from the tip part through the remainder of articulated segments to a control mechanism of the handle.

As the name indicates, endoscopes are used for seeing inside things, such as lungs or other human body cavities of a patient. Modern endoscopes are therefore typically equipped with a light source and a vision receptor including a vision or image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fiber, may provide illumination.

Additionally, when, as in the present disclosure, the insertion tube of the endoscope is intended to be inserted into a human body cavity, the insertion tube should furthermore be sealed in a watertight manner. This is particularly the case for a distal tip part accommodating a camera, LED(s), and/or other delicate electronics, prone to malfunction or destruction if exposed to humidity.

One known way of sealing the tip part of an endoscope is disclosed in WO2010/066790. In this document, a transparent monolithic housing is formed around the electronics and working channel by placing the electronics and the tube forming the working channel in a mold of transparent material, such as silicone. A transparent UV curable resin is then inserted from the bottom of the mold to avoid bubbles to form in the transparent resin. Because the resin rises slowly from the bottom, the air is slowly expelled from top of the mold, without any risk of air bubbles being trapped in the mold. The resin is then cured using UV irradiation through the transparent mold to form the monolithic housing.

Tip part fluid nozzles are known from the prior art. Such nozzles are typically formed by providing a metal blank and then milling out the fluid paths within the nozzle. Some prior art nozzles are positioned to project from a front surface of the tip part. Typically, a milled out metal nozzle element is attached to an exterior housing of the tip part. In use, the tip part is then connected to one or more fluid sources. The fluid provided from the fluid sources may be liquid, such as water, and/or gas, such as carbon dioxide. In some prior art tip parts, one nozzle is provided for ejection of both gas and liquid; in others, two separate nozzles are provided. Ejection of liquid from the nozzle is typically used for flushing a front surface or a camera window or light windows with liquid and thereby cleaning at least part of the front surface. Ejected gas may be used for cleaning remaining liquid on the camera window off after flushing with liquid, but is primarily used for expanding a body volume to improve the view through the camera.

SUMMARY OF EMBODIMENTS OF THE DISCLOSURE

A first aspect of this disclosure relates to a tip part for forming a tip of a disposable insertion endoscope, the tip part comprising: an exterior housing having an open proximal end for connection to other parts of the endoscope, such as an insertion tube, the housing further having a front wall, wherein a circumferential wall of the housing extends from a front end of the housing to the proximal end of the housing, the circumferential wall and the front wall enclosing an interior spacing accommodating a vision receptor able to provide an image from light received from an object to be investigated; and a camera window positioned at least partly in front of the vision receptor, the camera window being positioned in, positioned in front of, or forming part of the front wall so that light received from the object can pass through the window to the vision receptor; wherein the housing further comprises a nozzle provided at the distal end of the tip part for flushing an exterior surface of the window with a liquid transferred to the nozzle through a liquid conduit extending from the proximal end of the housing, through the interior spacing, and to the nozzle; and wherein the front wall and the circumferential wall are integrally formed from one polymer material and are in one piece with each other, and the front wall and the nozzle are integrally formed from said one polymer material and are in one piece with each other.

The tip parts according to this disclosure may make it possible to reduce external dimensions of the tip parts and may reduce costs and time in manufacture.

The tip of the disposable insertion endoscope may be a distal tip of the disposable insertion endoscope.

The front wall may be a distal front wall positioned oppositely from the proximal end and at least partly coinciding with a distal end of the tip part.

The circumferential wall of the housing may extend from the, potentially distal, front wall of the housing to the proximal end of the housing.

The nozzle may be provided at the distal end of the tip part.

The camera window may be an opening in the exterior housing or a transparent part in or of the exterior housing enabling light to enter into the tip part to be received by the image sensor.

The camera window may comprise a second material, which may be a second polymer material, and which may be different from said one polymer material of the exterior housing. The camera window and the exterior housing may be integrally molded in one piece by a multi-component molding process, which may be according to the methods according to the second aspect of this disclosure. A front surface of the camera window may be in the same plane as a front surface of the exterior housing.

The term "integrally formed in one piece" as used herein may involve that two or more parts are integrally molded in one piece with each other.

The exterior housing may be cup-shaped, the cup being formed by the front wall and the circumferential wall.

The nozzle may be a liquid nozzle or a nozzle for ejection of liquid and/or may be a gas nozzle or a nozzle for ejection of gas.

Said one polymer material may include or consist of one or several polymers and/or further materials. One or more of said polymers may be plastic or thermoplastic polymers. Said one polymer material and a potential second polymer material (see below) may be selected from thermoplastic materials, thermoset materials, and elastomers. The second material may comprise or consist of a transparent material and/or may include or consist of several polymers and/or further materials. Said one polymer material and/or said second polymer material may be fiber-reinforced. The first material may be opaque at least in a set condition. Said one polymer material may also be selected for other properties, such as good adhesion to sealant materials and adhesives. Thus, the set said one polymer material may have better adhesion properties to glue than the second polymer material.

The circumferential wall may have a cylindrical or circular-cylindrical outer and/or inner surface. The circumferential wall may comprise or be a circumferentially extending cylindrical wall.

The front wall of the housing may include a liquid outlet, which may be for introducing liquid into the nozzle. The front wall of the housing may include further outlets, inlets, and/or openings, such as a working channel opening and a water jet outlet for rinsing tissue.

The tip part may further comprise a bending section having a distal end segment, the distal end of the bending section and the proximal open end of the housing potentially being adjoined to each other.

A first window part and a second window part of the camera window may be molded as one single piece of a second polymer material.

The nozzle may be formed integrally with the front wall as a single piece of a first polymer material and/or integrally with said first and second window parts as a single piece of the second polymer material.

The first material may be opaque. This may allow the introduction of shading parts inter alia reducing stray light and glare into the vision receptor.

The first material may have better adhesion properties to glue than the second material. This may allow the circumferential wall of the housing to adhere efficiently to a sealing glue for sealing the interior spacing, and for an exterior sleeve or an outer sheath of the insertion tube of the endoscope to be securely adhered to the exterior or the interior of the circumferential wall of the housing.

The second material may be a thermoplastic material. This may allow the exterior housing to be produced in an efficient manner, such as by injection molding.

The molding tool may comprise a first mold cavity, a second mold cavity and a core. The first cavity and the second cavity may have generally cylindrical shapes.

The first material may be allowed to set before the at least one second material is introduced.

A volume of the at least one second material introduced in the mold may be smaller than a volume of the first material introduced in the mold.

The at least one second material may be selected from the group comprising thermoplastic materials, thermoset materials, and elastomers.

The at least one second material may comprise the transparent material.

The vision sensor may be a camera sensor of a camera. The vision sensor and camera may form part of a vision receptor, which may also include a lens stack and a printed circuit board (PCB). At least part of or all of the vision receptor may be accommodated in the exterior housing.

The circumferential wall may be a side wall and/or may have a substantially cylindrical shape. The front wall and window may be integrally formed or molded in one piece. The front wall and the circumferential wall may form a liquid-tight (except for any potential inlets, outlets, and openings) barrier or border between an exterior of the tip part or the environment and the interior spacing of the tip part. The exterior housing may also accommodate at least part of a working channel for supplying fluid to a working channel opening in the front wall, a PCB of the vision receptor, and/or the vision sensor or image sensor of a vision receptor.

By integrally forming the circumferential wall and window, a sealed tip part may be provided. Additionally, assembly of the tip part may be made simpler as fewer parts are required.

Additionally or alternatively, the exterior housing may essentially consist of the same material as the window, such as a transparent material.

This may provide the advantage that the first and second materials can be selected according to the desired properties, for instance a transparent material may be selected for the window and an opaque material may be selected for the exterior housing.

In this context and applying generally to this disclosure, the term "comprises" includes "consists essentially of". The multi-component molding process may be a two-component molding process.

The tip part may further comprise at least one light source for providing light to the object to be investigated, the light source potentially being accommodated in the interior spacing of the exterior housing.

The camera window may also extend to be positioned in front of the first light source, or a window part may include the camera window and one or more light windows as described further below. Alternatively, a light window provided separately from the camera window may be provided for the light source, the separate light window being provided in front of the light source, potentially in a distal front surface of the tip part.

The exterior housing may comprise a first polymer material and a second polymer material, the second polymer material being transparent, The exterior housing may comprise a first window part arranged in front of an electronic vision device in the field of view thereof and a second window part arranged in front of at least one light source.

The light source(s) may be optical fiber or a light emitting diode (LED).

The light source may be a first light source, and the tip part may comprise a second light source. The second light source may be provided in a manner similar to the first light source. The first light source may be positioned at a first lateral side of the vision sensor and/or receptor, and the second light source may be positioned on an opposite lateral side of the vision sensor and/or vision receptor.

The vision receptor may comprise one or more lenses, potentially arranged in a lens stack and arranged between the vision receptor and the camera window, potentially in the housing.

An exterior front surface of the tip part may be substantially planar, wherein the nozzle may project in a front or distal direction from a plane of the distal front surface. The circumferential wall may extend from the front surface, potentially along lateral sides of the vision sensor and/or vision receptor and the potential light source.

The circumferential wall may extend in a direction distally-to-proximally. The exterior front wall may extend in a transverse direction, the transverse direction being transverse to the distally-to-proximally direction.

The nozzle may include one or two or more fluid inlets and at least one fluid outlet. The one or more fluid inlets may be formed by outlets of respective fluid channels and/or fluid tubes as described further below.

The tip part, in particular the one or more fluid tubes, may be connected to or be connectable to one or more fluid sources. The fluid provided from the fluid sources may be liquid and/or air or gas. The liquid may be water. The gas may be carbon dioxide. Ejection of liquid from or a liquid jet ejected or sprayed from the nozzle may be used for flushing with liquid and thereby cleaning at least part of the front surface of the camera window. Ejected gas may be used for cleaning remaining liquid on the camera window off after flushing with liquid. The ejected gas may also be used for expanding a body volume. The gas may also be used for accelerating or otherwise affecting the liquid flow and/or the liquid flushing process.

The nozzle may comprise at least one nozzle outlet which may face towards the camera window. The nozzle outlet may include an outlet opening. The outlet opening may have a width in a direction extending along a front surface of the tip part and a depth extending in the proximal-distal direction. The outlet opening may be rectangular, in particular when viewed in a radial direction transverse to the proximal-distal direction towards the nozzle outlet. The outlet opening may include rounded corners. The nozzle outlet may, when seen towards a front surface of the tip part, have an outwardly rounded shape, which may increase an opening area of the outlet opening compared to if the shape were linear. This rounded shape may be formed by an edge of a nozzle roof, this edge forming a top edge of the nozzle opening. Beneath the roof, in the proximal direction, a bottom edge may be formed by a nozzle floor or, if no nozzle floor is present, by an edge of a plane front surface of the exterior housing.

The nozzle may have a low depth, which may be measured from the bottom edge to the top edge, compared to its width. A proportional relationship of depth:width may be from 1:2 to 1:12, in particular from 1:3 to 1:11, 1:4 to 1:10, 1:4 to 1:9, 1:5 to 1:9, 1:6 to 1:9 or 1:7 to 1:9. The depth may be from 0.1 to 0.3 mm, in particular from 0.15 to 0.25 mm. The width may be from 1 to 2.2 mm, in particular from 1.3 to 1.9 or 1.4 to 1.8 mm. This may provide a flat jet that may be used to flush the entire camera window, including potential light windows, especially if the hand fan shape as described below is also applied.

The nozzle may comprise a nozzle roof with an interior roof surface facing in the proximal direction. The nozzle roof may extend to the nozzle outlet. The roof may have an opposed exterior surface facing in the distal or front direction. The interior roof surface may be positioned at least partly above the nozzle inlet(s) and/or may extend to the nozzle outlet and may be inclined towards a plane of the camera window or a distal front surface of the tip part. The interior roof surface may comprise a fin projecting in the proximal direction, which fin may be positioned centrally in a flow direction towards the nozzle outlet.

The nozzle may comprise a nozzle floor positioned opposed to the nozzle roof in the distal direction where the nozzle floor may form part of a distal front surface of the tip part. A surface of the nozzle floor may face outwardly, in the distal direction and/or in a front direction of the tip part.

Alternatively, the nozzle may not comprise such a nozzle floor. In this case one or more of the fluid nozzle inlets may be positioned at least partly directly beneath (in the distal direction) the nozzle roof. This may make it possible to mold the nozzle in one piece with the exterior housing front surface.

Lateral side walls of the nozzle may extend between and connect the nozzle roof with the nozzle floor and/or may extend between and connect the nozzle roof with a distal front surface of the tip part. One of these side walls may be a back wall positioned opposed to the nozzle outlet, and may include a transitional section providing a transition from the distal front surface of the tip part to the nozzle roof.

An interior surface of this back side surface may be rounded or form a curvature, or may be non-straight and include no steps, in a transition of a fluid flow from the fluid channel(s) to the flow ejected from the nozzle outlet towards the camera window, which may be an advantage in terms of the fluid flow through the nozzle. This distal front surface may be parallel with the roof and may be positioned farther in the distal direction than the nozzle roof so that the nozzle projects from this front surface in the distal direction. Two lateral interior side surfaces of associated lateral nozzle side walls provided on each side of the back surface may be arranged to form a flow path formed as a hand fan or a Japanese fan and/or a flow path of flow inside the nozzle towards the nozzle outlet may expand laterally along these lateral interior side surfaces. Accordingly, a fluid jet ejected from the nozzle outlet may be relatively flat in the distal-proximal direction and may expand towards the camera window, potentially shaped as a hand fan or a Japanese fan. Hereby, an advantageous flow path may be provided, which may potentially extend to an entire front surface of the camera window and potentially of one or light windows. A flow velocity of fluid flow may decrease towards the nozzle outlet.

The tip part may additionally or alternatively comprise a working tube which potentially forms part of a working channel of an endoscope. The exterior housing may accommodate at least part of the working tube. The working tube may be sealed in relation to the exterior housing, potentially so that fluid in the working tube may not ingress into the interior of the exterior housing. The working tube may include a working outlet opening, which may be positioned in a distal front surface of the exterior housing.

The vision receptor may comprise a vision sensor, such as an image sensor, such as of a camera module. The vision receptor may comprise a lens or a plurality of lenses potentially arranged successively and optionally in a casing. The plurality of lenses may be arranged, potentially in a lens stack, in front of the vision sensor, potentially so that an optical axis of the lens, potentially of the plurality of lenses, align or coincide with an optical axis of the vision sensor. A front or distal lens may form the camera window. The plurality of lenses may be spaced apart by at least one spacer, potentially a plurality of spacers. The vision receptor may comprise a printed circuit board (PCB) having at least one electrical component for converting light received by the vision receptor to an image. The exterior housing may accommodate a printed circuit board.

The camera window may have different shapes, such as circular, half-moon shaped etc. The camera window may comprise a plurality of window parts. The window parts may abut each other. The window parts may be fixed to each other, potentially by gluing or welding. The camera window may form part of the exterior housing. The camera window may be integrally formed or molded in one piece with the exterior housing. The camera window may be formed by a lens, potentially a front lens of a lens stack, of the vision receptor in which case this lens may be positioned in an opening of the housing.

Additionally or alternatively, the camera window may be a distal front window, potentially allowing the vision sensor to receive image information from the distal end of the tip part. An exterior surface of the camera window may form part of a distal front wall of the exterior housing.

Additionally or alternatively, the camera window may be a side window, for instance when the endoscope is a duodenum endoscope. In this case, the front wall may be a side front wall positioned at a lateral side surface of the tip part. The side window may allow the vision sensor to receive image information from a side, potentially from a radial direction, of the tip part. The exterior surface of the window may be an exterior side surface. Accordingly, the front wall may be a side front wall instead of a distal front wall.

Additionally or alternatively, the camera window may comprise a front window and a side window. Accordingly, the front wall may be both a distal and a side front wall.

The camera window may comprise, potentially consist essentially of, a transparent material. A transparent material can transmit some image information and may potentially be defined as allowing at least 50% of visible light entering the window at the exterior surface to pass through the window. The transparent material may be a polymer, glass, plastic polymer, or any other suitable material, e.g. silicone, or a combination thereof.

In this specification, the term "to accommodate" may additionally or alternatively be defined as "to house" or "to enclose" or "to surround". For instance, the exterior housing may enclose or surround the vision sensor and/or the light source.

In this specification, the terms "integrally" or "integrally provided" or "integrally comprising" or similar may be defined as the associated features forming an integral part of a whole; and/or are in one piece, potentially molded in one piece; and/or are substantially inseparable by hand.

In this specification, the term "proximal" may be defined as being closest to an operator of the endoscope, and the term "distal" as being remote from the operator. The term "proximal-distal" may be defined as extending between these two extremes, in the present case proximal-distal may extend along a center axis of the tip part extending between a proximal extremity of the proximal end of the tip part and a distal extremity of the distal end of the tip part.

In this specification, the distal end of the tip part should not be construed to only comprise the most distal extremity of the tip part, rather the term "distal end of the tip part" should be understood as a portion of the tip part being distally positioned, e.g. a remaining portion of the tip part relative to the proximal or back end and/or a portion of the tip part for not being connected to other parts of the endoscope and/or a distally located half of the tip part. In some embodiments, the window may be a side window positioned at the distal or front end of the tip part.

In this specification, the term "interior" may be defined as being positioned in an interior space of the tip part, and the term "exterior" may be defined as being positioned in an exterior space of the tip part or as not being positioned in an interior space of the tip part. The exterior housing may include an exterior surface that forms an outer surface of the exterior housing or the tip part.

In this specification, an endoscope may be defined as a device adapted for viewing body cavities and/or channels of a human and/or animal body. The endoscope may for instance be a conventional flexible or steerable endoscope or a rigid endoscope or an endotracheal tube potentially provided with a camera and light source for ensuring the correct position of the endotracheal tube, for instance a laryngoscope. The endoscope may be a duodenum endoscope or a ureteroscope, or, in particular, a gastroscope or a colonoscope.

Additionally or alternatively, the vision receptor comprises a casing, potentially in the form of a lens barrel, positioned between the first light source and a vision sensor of the vision receptor, the casing potentially including a light shield configured to substantially prevent light from passing through the casing.

The casing may encase the vision sensor and/or a lens or lenses of the vision receptor. The casing may extend along a proximal-distal axis of the tip part. The casing may be in the form of a lens barrel potentially substantially having the shape of a cylindrical shell. The light shield may be provided in the form of a light shielding layer provided on the casing. The light shielding layer may be provided by an adhesive, potentially hardened glue. The glue may be opaque, potentially black.

Additionally or alternatively, the camera window is positioned at a distal end of the tip part.

Additionally or alternatively, the vision receptor may comprise a lens, potentially a plurality of lenses, being arranged, potentially successively in the casing, between the vision receptor, potentially the image sensor or vision sensor, and the camera window.

Additionally or alternatively, the lens or plurality of lenses may be provided separately from the camera window. Additionally or alternatively, the lens or plurality of lenses is not an integral part of the camera window. Additionally or alternatively, the lens or plurality of lenses is made of a material different from a material of the camera window.

Additionally or alternatively, the camera window comprises a first light guide positioned in front of the first light source, potentially directly in front of the first light source.

Additionally or alternatively, The first light guide may be of a transparent material, potentially the same material as the window. The first light guide may have a predetermined length between at least one first light reception end adapted for receiving light from the first light source and at least one second light emission end adapted to emit light. The first light guide may form an integral part of the exterior housing and/or the camera window. By integrating the light guide in the exterior housing, it becomes possible to provide a sealed front end of the tip part and at the same time provide a well-defined exit viewing angle for the light from the light source.

In an embodiment, the front wall and the circumferential wall are integrally molded in one piece with each other, and the front wall and the nozzle are integrally molded in one piece with each other.

Alternatively, either the front wall and the circumferential wall are integrally molded in one piece with each other or the front wall and the nozzle are integrally molded in one piece with each other.

In an embodiment, two fluid channels for providing fluid to the nozzle are formed integrally in one piece with the exterior housing.

The two fluid channels for providing fluid to the nozzle may be molded integrally in one piece with the exterior housing.

A first of the two fluid channels may be for gas, a second for liquid.

The first fluid channel may extend farther towards the nozzle in the distal-proximal direction than the second fluid channel.

An inner diameter or largest cross section of one or both fluid channels may be 1.3 to 1.9 mm or 1.4 to 1.8 mm or 1.5 to 1.7 mm.

A fluid tube, which may alternatively be denoted a fluid pipe, may be positioned in each of the fluid channels. Each tube may extend through the tip part, potentially to respective fluid sources. Each tube may be provided separately from or not in one piece with the exterior housing. A first of the fluid tubes may be for gas, a second of the fluid tubes may be for liquid.

Positioning of tubes in the fluid channels may occur subsequent to manufacture of the exterior housing including the nozzle and potentially the camera window. The tubes may be inserted into the fluid channels in a distal to proximal direction, potentially through a proximally positioned opening of the exterior housing.

The first fluid tube may extend farther towards the nozzle in the distal-proximal direction than the second fluid tube.

An outer diameter or largest outer cross section of an outer surface of each fluid tube may correspond to the diameter or largest cross section of each corresponding fluid channel and may accordingly be 1.3 to 1.9 mm or 1.4 to 1.8 mm or 1.5 to 1.7 mm. An inner diameter or largest inner cross section may be 1 to 1.4 mm or 1.1 to 1.3 mm.

One or both tubes may have a constant diameter along its/their length(s). The tubes may be flexible and may comprise or consist of a plastic or polymer material, such as PET, PE or PP. The tubes may be tubular and may be cylindrical.

In a further development of the present embodiment, the nozzle comprises at least part of a fluid joint, the fluid joint joining flow paths extending through the fluid channels.

The fluid joint may join outlets from the fluid channels or fluid tubes.

The fluid joint may be formed and/or molded integrally in one piece with the exterior housing.

Including the fluid joint in the tip part may generally make it possible to enable e.g. an insertion tube of an endoscope, which may be a critical dimension, to be smaller in the radial direction.

The fluid joint may be at least partly formed by the nozzle, and/or the two fluid flow paths may be joined at least partly within the nozzle. This may save space within the exterior housing, making it possible to provide a tip part with a smaller radial extent. Alternatively, a further fluid tube or channel collecting the two fluid paths may extend from the tube joint to the nozzle.

Providing the fluid joint integrally, potentially molded integrally, in one piece with the exterior housing, potentially with either of or both of the exterior housing front surface and circumferential wall, may shorten the dead space in the tubes and may also make it possible to mix gas and liquid, potentially within the nozzle.

In another or further development of the present embodiment, at least part of the two fluid channels extend side-by-side and include an open slot extending longitudinally between them.

The open slot may allow for the two fluid tubes to be positioned close to, potentially abutting, each other along a longitudinal direction when the fluid tubes are positioned in the fluid channels.

Potentially, parts of the fluid channels along a longitudinal direction may be coinciding and/or parts of circumferential walls may be removed from the cut-outs where the fluid channels intersect each other. Accordingly, outlets from two fluid tubes and/or the inlets of the nozzle may be shaped like the number "8", especially if the fluid tubes have a rounded or circular cross section. This embodiment may make it possible to minimize dimensions of the fluid channels and/or fluid tubes since they are positioned very close to each other. This may, in turn, allow for a reduction of a total cross-sectional or radial extent of the tip part and/or the exterior housing.

This embodiment may also make it possible or at least easier to mold the fluid channels since there is a connection between them.

Another or further development of the present embodiment comprises two fluid tubes provided separately from the fluid channels, wherein one of the two fluid tubes is positioned in each of the two fluid channels.

The fluid tubes may be provided as any one of the fluid tubes described previously.

In another or further development of the present embodiment, a fluid outlet from each of the fluid tubes terminates at or in the nozzle so that they form fluid inlets into the nozzle.

The fluid tubes may terminate to form the joint described previously.

In an embodiment, a distal front surface of the tip part includes the camera window, two fluid inlets extending into the nozzle, and a working channel opening, wherein the camera window, the two fluid inlets, and the working channel window are equally distributed on the front surface in a circumferential direction of the tip part.

In an embodiment, a first nozzle fluid inlet to the nozzle is positioned closer to the camera window than a second nozzle fluid inlet to the nozzle.

The first fluid inlet may be for gas, and the second fluid inlet may be for liquid.

The nozzle may generally be suitable for ejection of both gas and liquid. The nozzle outlet may generally be for ejection of both gas and liquid.

A fluid flow path within the nozzle for fluid from the second nozzle inlet may cross a fluid flow path within the nozzle for fluid from the first nozzle inlet.

This embodiment may especially be combined with one or more of the options regarding the shape of the interior nozzle surfaces defining the fluid flow. A rounded shape of a flow path of the gas may generally be less important than that for the flow path of the liquid.

The nozzle fluid inlets may be positioned next to each other along a straight line in a cross-sectional or radial direction of the tip part, and the nozzle outlet may also be positioned along this line. The nozzle gas inlet may be positioned between the nozzle liquid inlet and the nozzle outlet. Hereby, the liquid flow path may intersect the gas flow path within the nozzle. A camera window center part may also be positioned along the line, allowing fluid to be sprayed from the nozzle outlet to the camera window.

The nozzle outlet may generally face and provide a flow path from the outlet along or in a cross-sectional or radial direction of the tip part. This may allow the flow from the nozzle outlet to reach the camera window.

An embodiment of the tip part further comprises a window part positioned at or in the front wall, wherein the window part comprises the camera window, and the window part is formed of a second polymer material, the second polymer material being different from said one polymer material.

The second polymer material being different from said one polymer material may involve that a composition of the two polymer materials is different and/or that the one polymer material comprises at least one component not included in the second polymer material, or reversely. For example, the one polymer material may comprise a polymer not included in the second polymer material, and/or reversely, and/or the one polymer material may comprise a specific polymer in one amount and the second polymer material comprises the same specific polymer in a different amount. Various physical or chemical properties, such as melting point and/or adhesive properties may similarly be different in the two polymer materials.

Alternatively, the window part is formed of the same material as the exterior housing, i.e. of the said one polymer material, which may in this case be transparent and/or translucent.

The window part may form part of the exterior housing or may be provided separately from the exterior housing.

The exterior housing may have been or may be manufactured in a two-component molding process, whereby the window part or camera window can potentially be said to be integrally molded in one piece with the front wall, the circumferential wall, and the nozzle.

The window part may be positioned in a cut-out of the distal end wall and/or may extend into a cut-out of the circumferential wall.

The window part may further include one or more, such as two, light windows for distribution of light from light sources positioned within the spacing of the exterior housing. The camera window and the light window(s) may be integrally formed in one piece with each other, the light window(s) potentially being integrally molded in one piece with the camera window.

The window part and/or the camera window may be transparent and/or translucent. The light window(s) may similarly be transparent and/or translucent and/or may allow light from an object to be investigated to pass through the light window(s) to illuminate the object to be investigated. The object to be investigated will typically be provided in front of or distal to the front wall, the camera window, and the light window(s).

The camera window may generally be positioned with a center line of the camera window coinciding with a center line of a distal front surface of the tip part or of the exterior housing. Two light windows may be positioned one on each side of the camera window, potentially with an equal distance to the center lines.

The nozzle may be provided, and the nozzle outlet positioned, so that a nozzle fluid jet ejected from the nozzle may, potentially directly, reach both the camera window and the light window(s).

An embodiment of the tip part further comprises a light guide positioned in front of a light source.

The light guide may be positioned behind or proximally from the light window of the previous embodiment.

One or further light guides may be provided, each potentially being positioned behind or proximally from a light window.

The window part of the previous embodiment may comprise the light guide(s). The light guide(s) may thus be formed of the second polymer material.

Alternatively, the light guide is provided separately from the window part and/or of the same material as the exterior housing, i.e. of the said one polymer material, which may in this case be transparent.

The light guide(s) may form part of the exterior housing or may be provided separately from the exterior housing.

The exterior housing may have been or may be manufactured in a two-component molding process, whereby the window part including the light guide(s) can potentially be said to be integrally molded in one piece with the front wall, the circumferential wall, and the nozzle.

The light window may be a distal end of the light guide.

The light guide(s) may extend in a proximal direction into the interior spacing of the exterior housing.

The camera window and/or the light window(s) and/or the light guide(s) may be integrally formed in one piece with each other, these parts potentially being integrally molded in one piece. The light guide(s) are transparent.

In another aspect, the present disclosure involves a method of manufacture of tip part for forming a tip of a disposable insertion endoscope, wherein the tip part comprises: an exterior housing having an open proximal end for connection to other parts of the vision device, such as an insertion tube of an endoscope, the housing further having a front wall, wherein a circumferential wall of the housing extends from a distal end of the housing to the proximal end of the housing, the circumferential wall and the front wall enclosing an interior spacing accommodating a vision receptor able to provide an image from light received from an object to be investigated; and a camera window positioned at least partly in front of the vision sensor, the camera window being positioned in, positioned in front of, or forming part of the front wall so that light received from the object can pass through the window to the vision sensor; wherein the housing further comprises a nozzle for flushing an exterior surface of the window with a liquid transferred to the nozzle through a liquid conduit extending from the proximal end of the housing, through the interior spacing, and to the nozzle; said method comprising: integrally molding the exterior housing in one piece so that the front wall and the circumferential wall are molded in one piece with each other and so that the front wall and the nozzle are integrally molded in one piece with each other.

The present disclosure also involves a method of manufacture of tip part for forming the distal tip of a disposable insertion endoscope, wherein the tip part comprises: an exterior housing having an open proximal end for connection to other parts of the vision device, such as an insertion tube of an endoscope, the housing further having a front wall, wherein a circumferential wall of the housing extends from a distal end of the housing to the proximal end of the housing, the circumferential wall and the front wall enclosing an interior spacing accommodating a vision sensor able to provide an image from light received from an object to be investigated; and a camera window positioned at least partly in front of the vision sensor, the camera window being positioned in, positioned in front of, or forming part of the front wall so that light received from the object can pass through the window to the vision sensor; wherein the housing further comprises a nozzle for flushing an exterior surface of the window with a liquid transferred to the nozzle through a liquid conduit extending from the proximal end of the housing, through the interior spacing, and to the nozzle; said method comprising the step of: integrally forming the exterior housing in one piece so that the front wall and the circumferential wall are formed in one piece with each other and so that the front wall and the nozzle are integrally formed in one piece with each other.

The methods according to this aspect of the present disclosure may be methods of manufacture of a tip part according to any one, or any combination, of any one of the embodiments of tip parts as disclosed herein. The methods according to this aspect of the present disclosure may additionally or alternatively comprise any of the further method steps as disclosed herein, including those disclosed in relation to the tip parts of the present disclosure.

The molding step may involve or consist of injection molding. Injection molding is typically efficient in terms of quick reproduction of identical items.

The first and/or second material may be selected from thermoplastic materials, thermoset materials, and elastomers. The second material may comprise or consist of a transparent material. The first material may be opaque at least in a set condition. The first material and said one polymer material may also be selected for other properties, such as good adhesion to sealant materials and adhesives. Thus, the set first material may have better adhesion properties to glue than the second material or the second polymer material.

The second material may be transparent and/or may include the camera window and potentially one or more light windows and/or may be provided as disclosed herein with respect to the description of the tip parts of this disclosure.

The methods according to this disclosure may comprise introduction or positioning of one or more components, such as tubes, the vision sensor, the vision receptor, light sources etc., into the spacing of the exterior housing, optionally subsequent to manufacture of the exterior housing.

The methods according to this aspect of the present disclosure may further comprise the steps of, and/or a method of manufacture of the tip parts according to this disclosure may comprise: providing a molding tool; introducing a first melted material into the molding tool, wherein the first material may be said one polymer material on a melted form; introducing at least one second melted material different from the first material into the molding tool, wherein the second material may be said second polymer material on a melted form; allowing the second material to set and form a combined external housing with the first material; and removing the combined external housing from the molding tool.

This may allow the provision of an integrated unit for the tip external housing having different areas with different desired properties; specifically, the second material may form the camera window and potentially one or more light windows.

The molding tool may comprise a first cavity, a second cavity, and one or more cores. If applying injection molding, this may be advantageous since the molded object may shrink during cooling and therefore may tend to stick to the core. The first material may be allowed to set or partly set before the second material is introduced. This may provide well-defined boundaries between the two materials in the final integrated unit. Moreover, it may allow the first mold to stick to the core for the introduction into the second cavity of the molding tool. The volume of the second material introduced in the mold may be smaller than a volume of the first material introduced into the mold. This may be of advantage if the second material is more brittle than the first material because having a smaller volume thereof will make it less prone to stick to the mold due to shrinking, thereby making it easier to extract from the mold. Accordingly, the second material may also be injected at higher pressure than the first material because a high pressure used for the first material will make it more prone to sticking to the mold and/or core(s), in turn making removal more difficult. Accordingly, the introduction of the first and/or the second material may form part of an injection molding process.

The second material may comprise or consist of a transparent material. Injecting the transparent material as the second material may be advantageous because transparent materials, which are preferred for their optical properties, may then be introduced under higher pressure than the first material. This, in turn, may reduce shrinking and may provide improved control of the optical properties of the manufactured tip part. The second material, which may be more brittle, may generally constitute only a minor part of the total material of the exterior housing. This may make it is easier to remove the exterior housing from the mold. The first material may accordingly be opaque at least in its set form. The first material and said one polymer material may alternatively or additionally be selected for other properties, such as good adhesion to sealant materials and adhesives. Thus, the set first material may have better adhesion properties to glue than the second material or the second polymer material. The first cavity and the second cavity may have generally cylindrical shapes. This may result in a generally cylindrical exterior housing which, in turn, may be suitable for endoscopes made with the tip part according to the present invention.

In an embodiment, the method further comprises the step of integrally molding the exterior housing and the camera window in one piece with each other in a multi-component molding process, in which molding process the exterior housing and the camera window are manufactured from two different materials.

Alternatively, in such a multi-component molding process, the window part is formed of the same material as the exterior housing, i.e. of the said one polymer material, which may in this case be transparent and/or translucent. In this case, either the exterior housing or the camera window may be manufactured with master batch, the other without.

In another aspect, the present disclosure involves an endoscope comprising a tip part according to any one of the embodiments of tip parts disclosed herein and/or comprising a tip part manufactured according to any one of the embodiments of methods of manufacture of a tip part as disclosed herein.

The endoscope may be a disposable insertion endoscope. The endoscope may include one or more features as described herein in the above, including the features described in the above introduction to this description, and in connection with the description of the methods and tip parts according to the present disclosure.

The endoscope may comprise an elongated insertion tube with a handle at the proximal end. The tip part may be positioned at the distal end of the elongated insertion tube. The tip part may further comprise a bending section positioned between the tip part and the elongated insertion tube. The bending section may be configured to be articulated to maneuver the endoscope inside a body cavity.

A person skilled in the art will appreciate that any one or more of the above aspects of this disclosure and embodiments thereof may be combined with any one or more of the other aspects and embodiments thereof.

BRIEF DESCRIPTION OF THE DRAWINGS

In the following, non-limiting exemplary embodiments will be described in greater detail with reference to the drawings, in which:

FIG. 3 shows a rear perspective view of the tip part of FIG. 2a;

FIG. 4 shows a side view of the tip part of FIG. 2a;

FIG. 5b shows an enlarged view of a portion of the cross-sectional side view of FIG. 5a;

FIG. 6b shows a front view of the tip part of FIG. 2a, including the enlarged portion thereof shown in FIG. 6a;

FIG. 7a shows an enlarged portion of a rear view of the tip part of FIG. 2 shown in FIG. 7b;

FIG. 7b shows a rear view of the tip part of FIG. 2, including the enlarged portion thereof shown in FIG. 7a;

FIG. 8b is a cross-sectional view of the camera of FIG. 8a;

DETAILED DESCRIPTION

Figure 1:
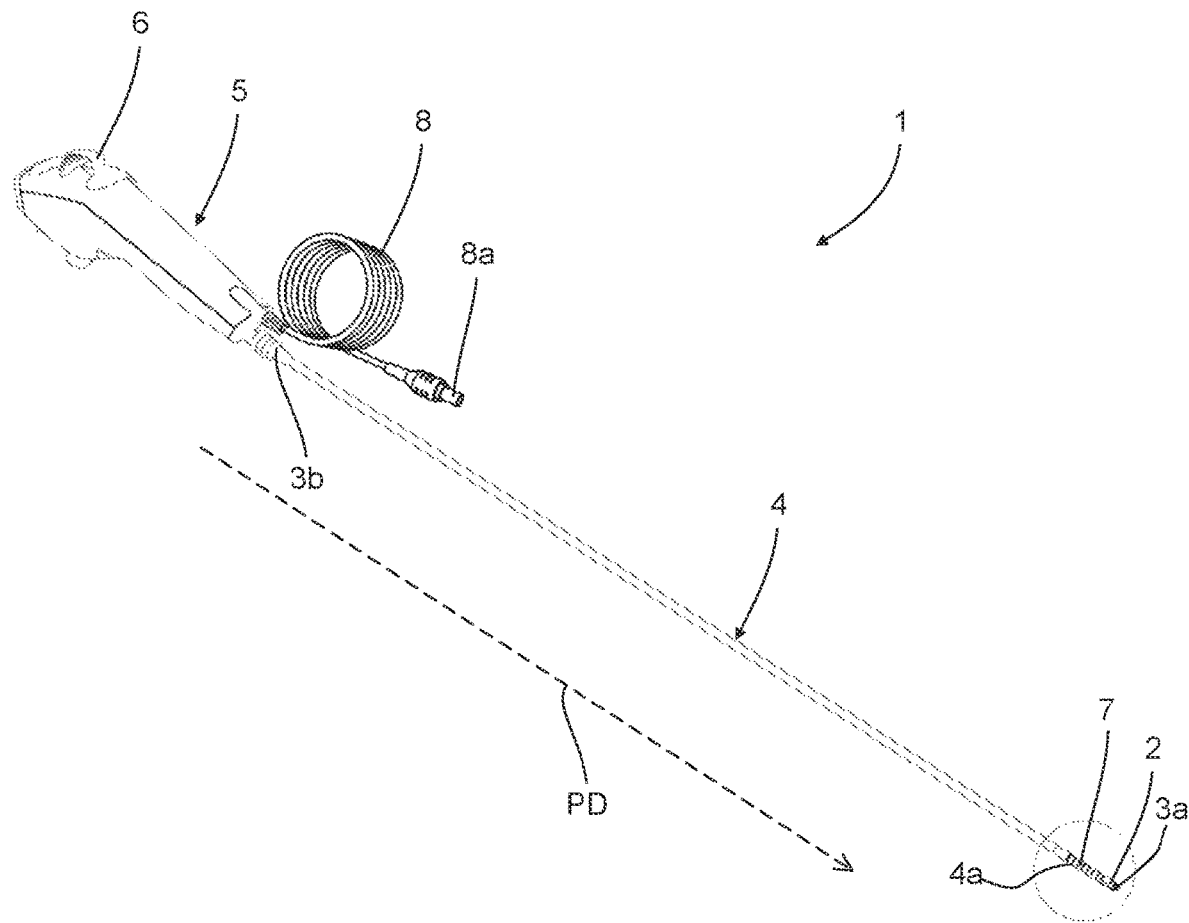
FIG. 1 shows an embodiment of a disposable insertion endoscope according to the present disclosure.

FIG. 1 shows an endoscope 1 including a distal tip with a tip part 2, the tip part 2 being an embodiment of the tip part according to the first aspect of the present disclosure. The tip part is manufactured according to the method of the present disclosure. The endoscope 1 may be disposable or designed for single-use and may be used in a variety of procedures from which the endoscope 1 takes its procedural name, such as gastroscope, but the endoscope 1 could also be used for other medical purposes.

In many respects, the endoscope 1 is of conventional design. For example, the handle, insertion tube, and camera (discussed below) may be of conventional design, except for the addition of the tubes and related components provided to supply fluids to the nozzle (discussed below). The tip part 2 is positioned at a distal end 3a of an elongated insertion tube 4 of the endoscope 1. The insertion tube 4 is at a proximal end 3b connected to a handle 5, which includes a control button 6 for controlling bending of a bending section 7 positioned near the tip part 2. In the shown embodiment, the bending section 7 is positioned between the tip part 2 and the insertion tube 4. The bending section 7 is configured to be articulated to maneuver the endoscope 1 inside a body cavity. An example of the bending section 7 is described with reference to FIGS. 9a and 9b. The handle 5 may be connected to fluid hoses (not shown) for supplying fluids from fluid supply sources, e.g. liquid and gas or air, to the tip part 2. The fluid supply sources may include one or more fluid pumps or other fluid drive means. The endoscope 1 or the insertion tube 4 defines a proximal-distal direction denoted as "PD" in FIG. 1. A cable 8 having a connector 8a is provided to electrically couple the endoscope 1 to a video monitor which is configured to display video images obtained with a vision sensor 36 (shown in FIG. 8b) of the endoscope 1.

Figure 2A:
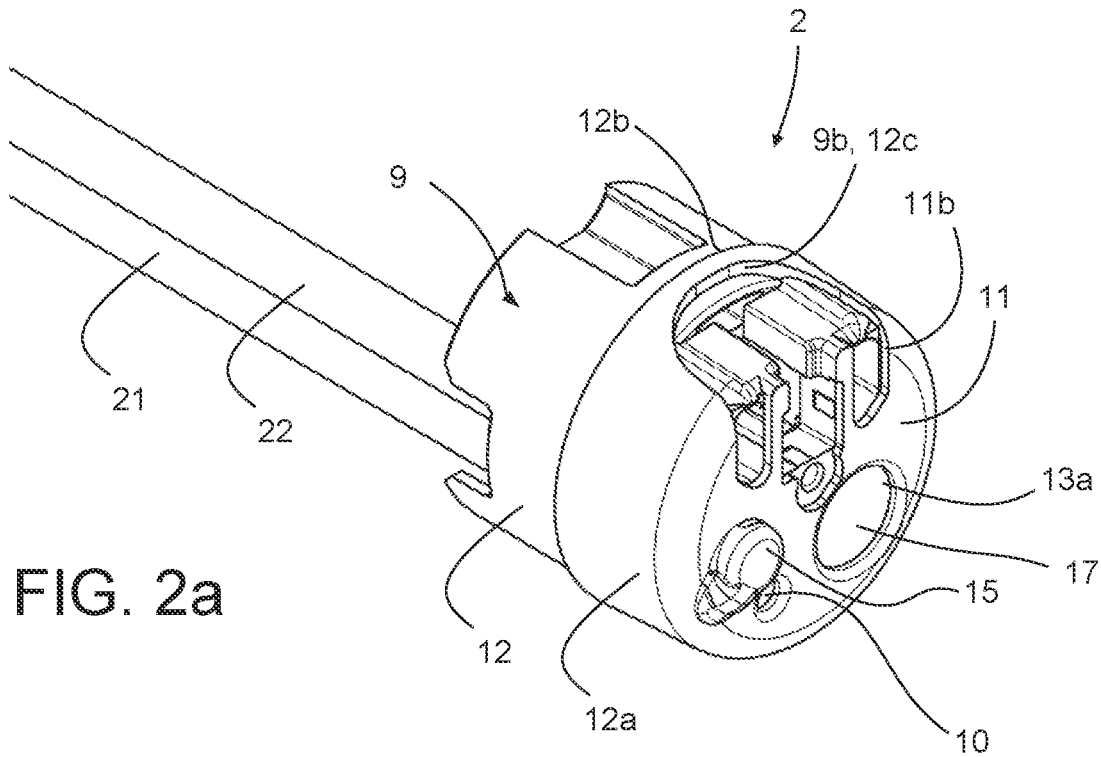
FIG. 2a shows a front perspective view of a tip part of the endoscope of FIG. 1 structured with a cutout adapted to receive a window.
Figure 2B:
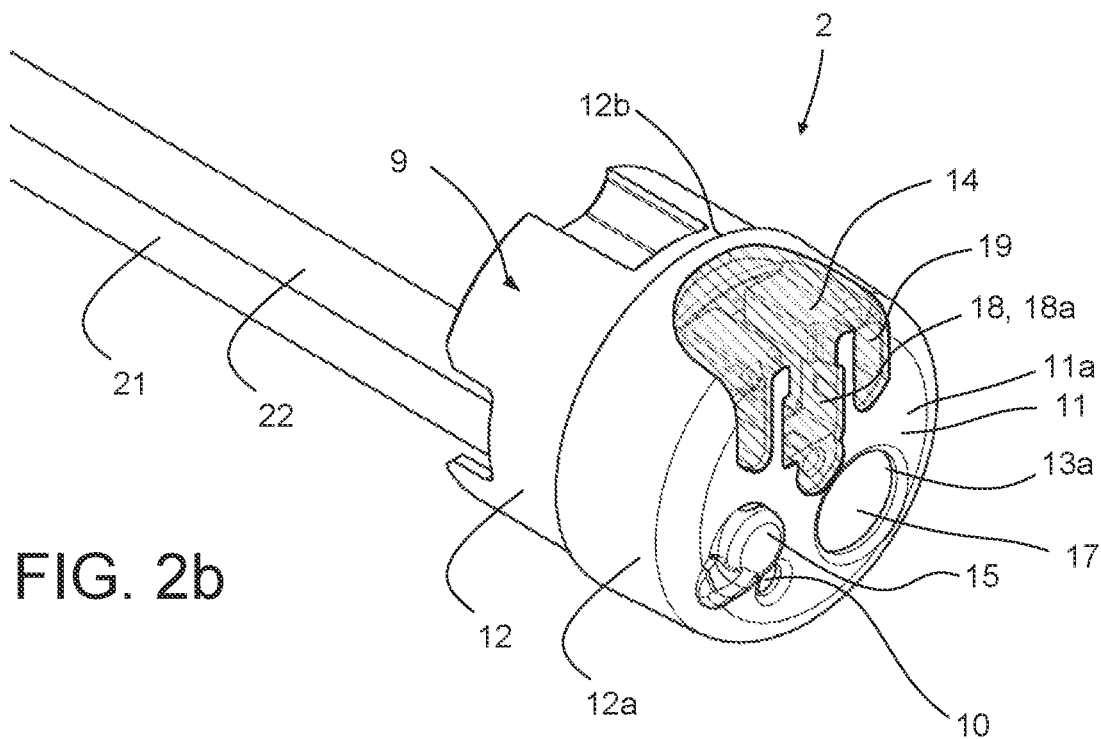
FIG. 2b shows the front perspective view of the tip part of FIG. 2a and including the window.
Figure 3:
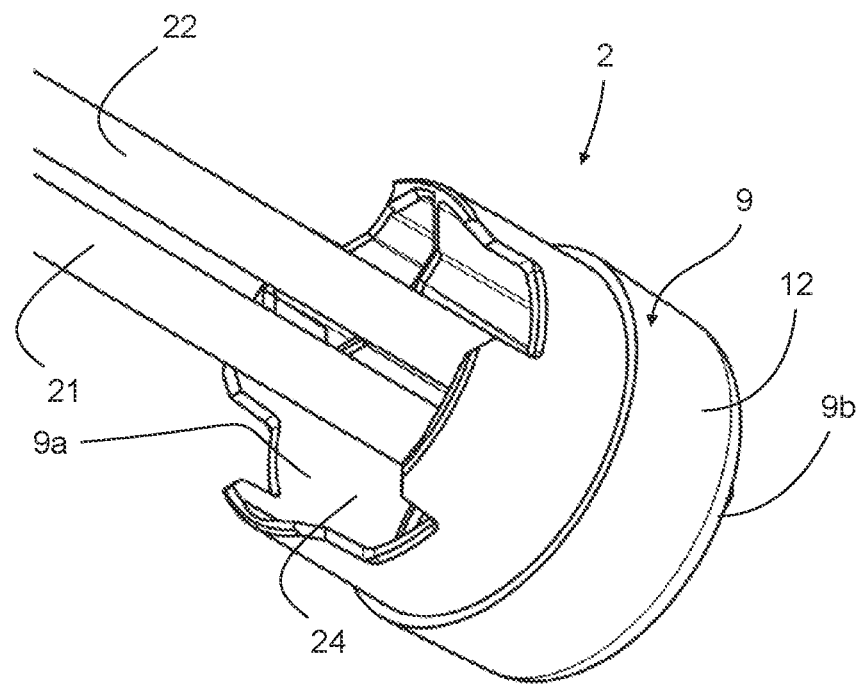
Figure 4:
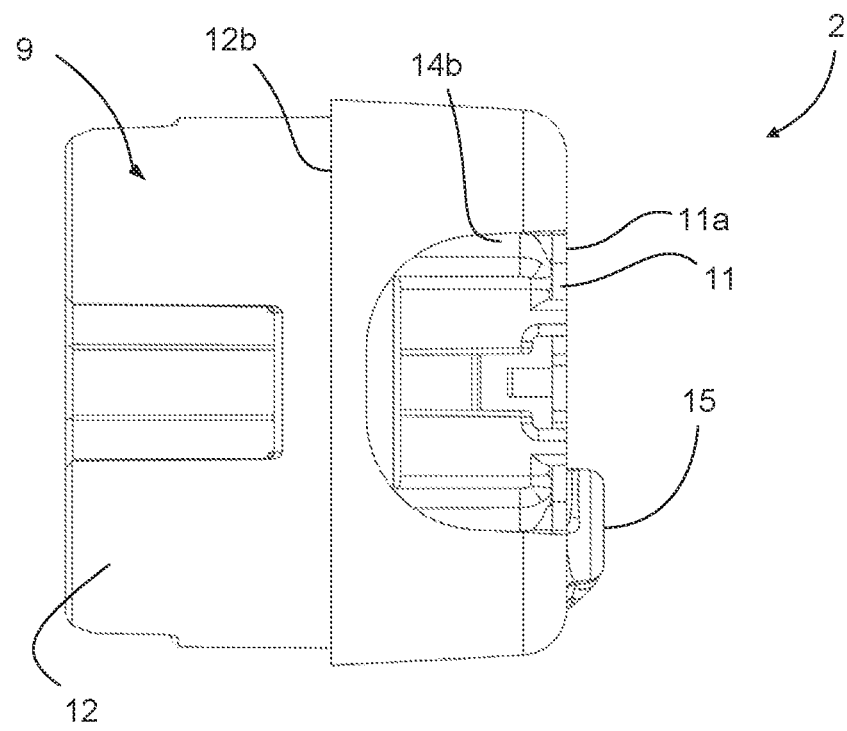

FIGS. 2a to 7 show different views of the tip part 2. Referring to FIGS. 2a, 2b, and 3, the tip part 2 includes an exterior housing 9 having an open proximal end 9a for connection to the more proximally positioned parts of the endoscope 1. The housing 9 further comprises a distal or front wall 11, wherein a cylindrically shaped circumferential wall 12 extends from a distal end 9b to the proximal end 9a of the housing 9. The circumferential wall 12 and the front wall 11 enclose an interior spacing 24 accommodating a camera 30 (shown in FIGS. 8a and 8b) including the vision sensor 36 and able to provide an image from light received from an object to be investigated. The front wall 11 is positioned oppositely from the proximal end 9a of the housing 9. The circumferential wall 12 extends from the front wall 11 to the proximal end 9a of the housing 9.

The housing 9 further comprises a nozzle 15 provided at the distal end of the tip part 2 for flushing an exterior surface 18a of a camera window 18 with a liquid transferred to the nozzle 15 from the fluid sources. The liquid flows through fluid tubes 21, 22 extending from the handle 5 to the nozzle 15. The nozzle 15 is a liquid nozzle for ejection of liquid and also functions as a gas nozzle for ejection of gas, as described further below.

The front wall 11 and the circumferential wall 12 may be integrally molded from one polymer material in one piece. The front wall 11 and the nozzle 15, similarly, may be integrally molded from said one polymer material in one piece. The front wall 11, the circumferential wall 12, and the nozzle 15 may be integrally molded from one polymer material in one piece. The front wall and the circumferential wall can be also be molded separately and then bonded together to form a one-piece part. Said one polymer material is opaque and consists of, or comprises or consists essentially of, a thermoplastic polymer. A window component 14

(discussed below) is manufactured of a second polymer material which is transparent and similarly comprises a thermoplastic polymer.

In FIG. 2a the front wall 11 and the circumferential wall 12 include a cutout 9b for the window component 14, which is inserted in the cutout, as shown in FIG. 2b, and includes light windows 19 located on either side of the camera window 18. Cutout 9b comprises a cutout 12c on the circumferential wall 12 and a cutout 11b on the front wall 11. Therefore the front surface of the tip part comprises a portion provided by the front wall 11 and a portion provided by the window component 14. Alternatively stated, the front wall 11 includes an opaque portion and a transparent portion comprised by the window component 14. The light source windows 19 allow light to be emitted by light sources to illuminate the object under observation.

The exterior housing 9 is generally cup-shaped, the cup being formed by the front wall 11 and the circumferential wall 12. The circumferential wall 12 is a circumferentially extending cylindrical wall which has a generally cylindrical outer surface 12a and includes a step 12b for positioning of a flexible external sleeve or outer sheath 4a which extends over the bending section 7 to the step 12b, surrounding part of the tip part 2.

The front wall 11 of the housing 9 includes a liquid and gas outlet 16a (shown in FIG. 5b) located distally of the liquid tube 21 and gas tube 22, which is an opening in the front wall 11 for introducing liquid and gas into the nozzle 15. The front wall 11 of the housing 9 also includes a working channel opening 17 and a water jet outlet 10 for ejecting a water jet for rinsing tissue. The tip part 2 also comprises a working tube 13a (further described with reference to FIG. 7b) defining a working channel opening 17 positioned in the distal front surface of the tip part 2.

Figure 9A:
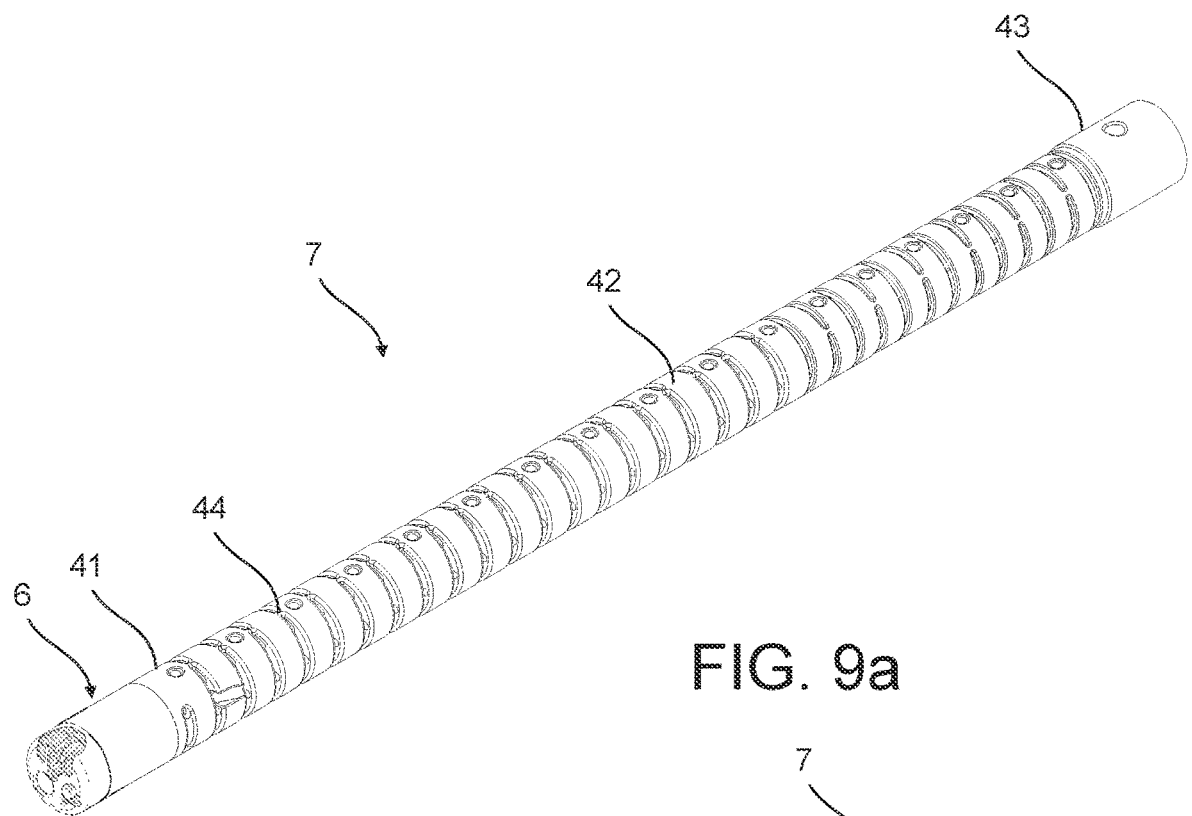
FIG. 9a is a perspective view of a bending section connected to the tip part.
Figure 9B:
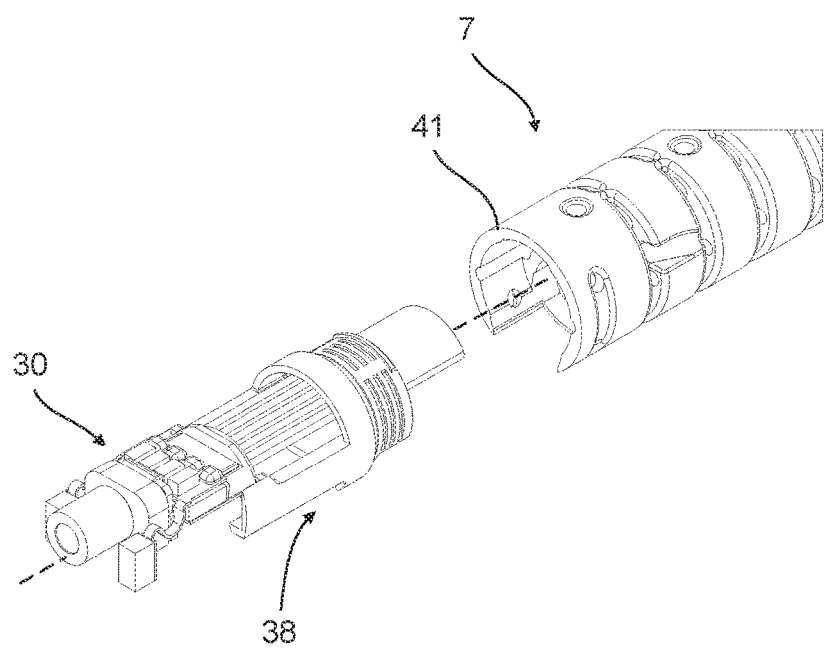
FIG. 9b is a exploded perspective view of a portion of the bending section and the camera.

The tip part 2 of the endoscope 1 further comprises the bending section 7, shown in FIGS. 9a and 9b, which has a distal end segment 41, intermediate segments 42, and a proximal end segment 43 interconnected by articulated sections 44 therebetween, the distal end segment 41 is connected to the proximal end 9a of the housing 9. An internal support 38 may be used to support the camera 30 inside the housing 9. The internal support 38 (shown in FIG. 9b) may include a proximal joint portion operable to form a joint with a complementary portion in the distal end segment 41 of the bending section.

Referring to FIG. 2b, the camera window 18 is positioned in the front wall 11 in front of the camera 30 so that light received from the object can pass through the camera window 18 to reach the vision sensor of the camera 30 as is conventional in endoscopes. The light windows 19 are positioned on the sides of the camera window 18 to permit light emissions therethrough to illuminate the object.

The camera window front surface 18a of the camera window 18 extends along the distal end surface of the tip part 2 in a plane common with a front surface 11a of the front wall 11. The window component 14 is also positioned so that its side surface extends into the circumferential wall 12 to have the side surface completing the cylindrical external surface of the circumferential wall 12. The window component 14 can potentially be said to form part of the exterior housing 9, a front surface of the window component 14 forming part of a front surface of the housing 9 or the front wall 11 thereof, and the side surface of the window component 14 forming part of the circumferential side surface of the housing 9 or the circumferential wall 12. Alternatively, the window component 14 can be said to be positioned in a cut-out 11b of the distal end wall 11 and extending into a cut-out 12c of the circumferential wall 12.

The window component 14 and the exterior housing 9 may be integrally molded in one piece by a multi-component molding process according to the methods of the second aspect of this disclosure, whereby the window component is integrally molded in one piece with the front wall 11, the circumferential wall 12, and the nozzle 15.

Alternatively, the window component provides side windows instead of the front windows discussed previously, for instance if the endoscope were a duodenum endoscope. In this variation, the camera is positioned with its optical axis aligned in a radial direction rather than the longitudinal direction. The side camera window is positioned in a cutout on the circumferential wall to allow the vision receptor to receive light reflected from an object located on a side of the tip part 2. The window component may also include light windows on the side and/or front of the tip part.

Referring to FIGS. 2a, 2b, and 3, fluid tubes 21 and 22 extend through the insertion tube 4 and are connectable to fluid sources (not shown) as described above. The fluids include liquid and gas. The liquid may be water and the gas may be carbon dioxide ($CO_2$). The fluids are ejected from the nozzle 15 to flush and clean at least part of the camera window front surface 18a of the camera window 18.

The nozzle 15 may be formed integrally with the front wall 11 as a single piece of the first polymer material. The first polymer material may be opaque, which limits stray light and glare from reaching the vision sensor. The first polymer material may have better adhesion properties to glue than the second polymer material to allow the circumferential wall 12 to adhere efficiently to a sealing glue sealing the interior spacing and for the outer sheath 4a to be securely adhered to the part of exterior surface of the circumferential wall 12 extending proximally from the step 12b. The first and second polymer materials are thermoplastic polymer materials which allows the exterior housing 9 and the window component 14 to be produced by injection molding in said two-component molding process with a liquid-tight seal formed at the juncture of the exterior housing 9 and the window component 14. Additionally, assembly of the tip part 2 is made simpler since fewer parts are required.

The distal exterior surface of the tip part 2, or front surface 11a, is substantially planar, the nozzle 15 projecting in a front or distal direction from a plane of the front surface. The circumferential wall 12 extends from this front surface in the proximal-distal direction, PD, shown in FIG. 1. The front wall 11 extends in a direction transverse to the direction PD.

Figure 5A:
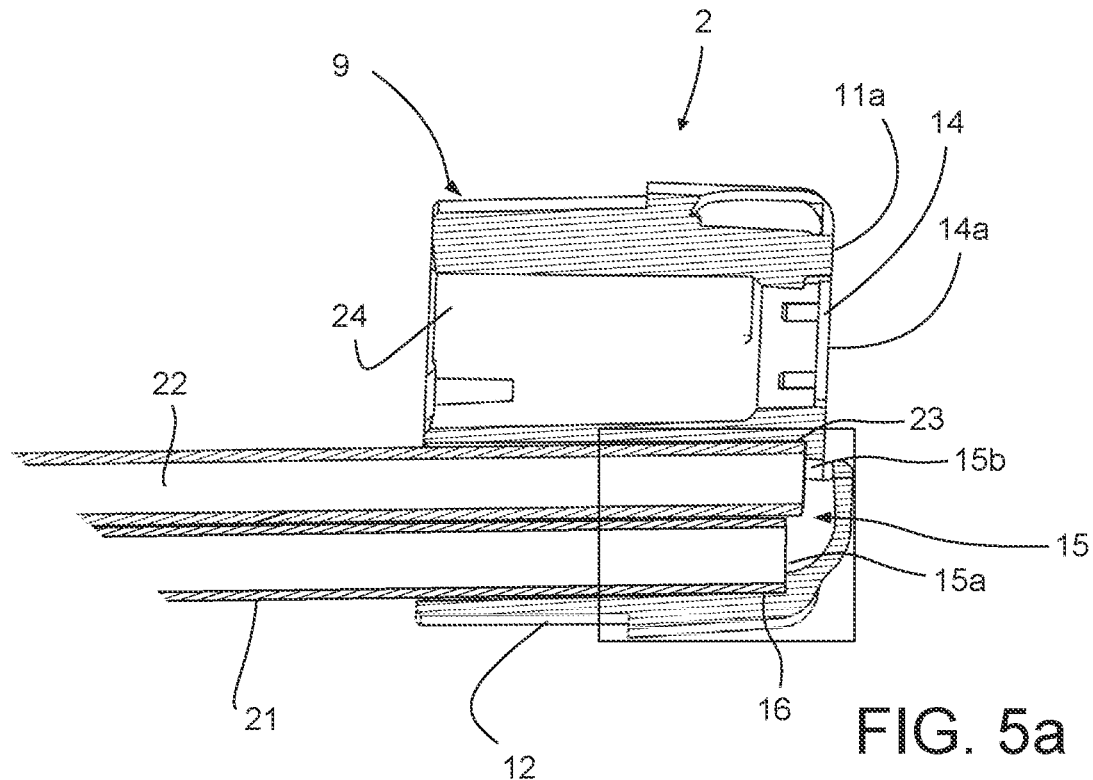
FIG. 5a shows cross-sectional side view of the tip part of FIG. 2a taken along the line V-V in FIG. 6, including an enlarged portion shown in FIG. 5b.
Figure 5B:
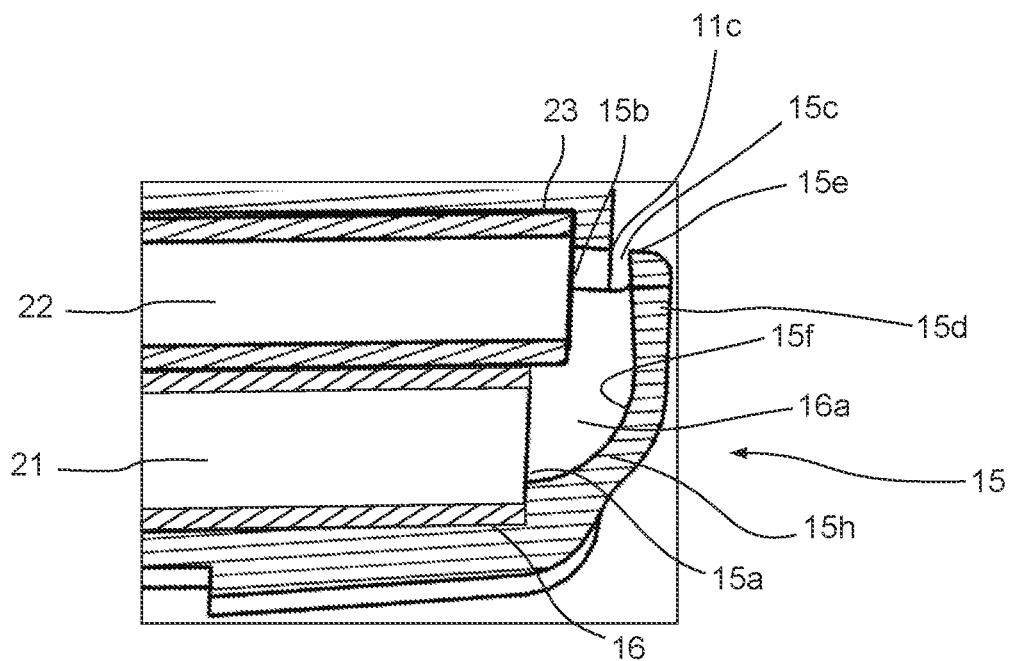

Referring to FIGS. 5a and 5b, the exterior housing 9 is formed with tube cavities, or channels 16 and 23, sized and shaped to receive the distal ends of the fluid tubes 21 and 22. In one example, the distal ends of the fluid tubes 21 and 22 form liquid and gas inlets 15a, 15b for the nozzle 15. In another example, the liquid and gas inlets 15a, 15b are molded in one piece with the exterior housing 9 distally of the tube cavities, and the fluid tubes 21 and 22 are inserted into the tube cavities 16, 23 to be adjacent the liquid and gas inlets. In either case, the fluid tubes provide fluid communication between the fluid sources and the liquid and gas inlets.

The tubes 21, 22 are positioned in an associated one of the channels 16, 23. Each tube 21, 22 extends from the tip part 2 to an associated fluid source as described above. Positioning of tubes 21, 22 in the channels 16, 23 occurs after molding of the exterior housing 9, the nozzle 15 and the camera window 14. The tubes 21, 22 are after this molding inserted into the fluid channels 16, 23 in the direction PD through the proximal opening 9a of the exterior housing 9. As shown, the gas tube 22 extends further distally than liquid tube 21.

The tubes 21, 22 each has a constant diameter, are flexible, and consist of a plastic polymer material with a tubular and cylindrical outer shape. An outer diameter of an outer surface of each fluid tube 21, 22 may be between about 1.3 to 1.9 mm, or 1.4 to 1.8 mm, or 1.5 to 1.7 mm, and preferably about 1.6 mm. An inner diameter of each fluid tube 21, 22 may be between about 1.0 to 1.4 mm, or 1.1 to 1.3 mm, and preferably about 1.2 mm.

The nozzle 15 includes the two fluid inlets mentioned above, in the form of a liquid inlet 15a and a gas inlet 15b. The nozzle 15 also includes a nozzle outlet 15c and a nozzle roof 15d extending across and spaced apart from the liquid and gas inlets 15a, 15b. The nozzle roof 15d has a nozzle roof edge 15e which defines, together with a front wall edge 11c of the front wall 11, the nozzle outlet 15c. An interior roof surface 15f extends to the nozzle roof edge 15e. The fluids discharged through the fluid inlets 15a, 15b impinge on and are redirected by the interior roof surface 15f toward the nozzle roof edge 15e. The nozzle roof 15d may extend toward the camera window 18 sufficiently such that in overlaps the front wall edge 11c. The nozzle roof 15d and the interior roof surface 15f may be angled toward the front wall surface 11a. The fluid inlets 15a, 15b can be considered as being at least partly coinciding with the fluid outlet 16a of the front wall 11 or as formed by outlets of associated liquid and gas tubes 21, 22.

The shape of the nozzle roof 15d and the corresponding nozzle outlet 15c, together with liquid and gas pressure and flow, can be designed and controlled to effect different fluid plumes for different effects. Ejection of the water from the nozzle 15 can be used for flushing and cleaning at least part of the camera window front surface 18a. Ejected gas can be used for cleaning remaining liquid on the camera window front surface 18a off after flushing with water. The ejected gas can also be used for expanding a fluid volume or for accelerating or otherwise affecting the liquid flow and/or the liquid flushing process.

The nozzle outlet 15c faces toward the camera window 18 and has a depth in the PD direction and a width measured along a plane perpendicular to the PD direction. The nozzle outlet 15c profile may be rectangularly shaped with rounded corners, see FIG. 4. The nozzle outlet 15c has, when seen towards the distal front surface of the front wall 11, an outwardly rounded shape which forms a circle section, which increases an opening area of the outlet opening compared to if the shape were linear, see FIG. 6.

The nozzle outlet 15c has a small depth, measured from the bottom edge 11c to the roof edge 15e, compared to its width. The depth may be between about 0.15-0.25 mm, preferably about 0.20 mm, and the width may be between about 1.4-1.8 mm, preferably about 1.6 mm, resulting in a depth to width ratio of between 1:5.6-1:12 and preferably about 1:8. The shape of the nozzle outlet 15c provides a flat, hand fan shaped fluid jet that can be used to flush the entire camera window front surface 18a and the front surfaces of the light windows 19. As mentioned, the inner diameter of one or both tubes 20, 21 may be between about 1.3 to 1.9 mm, or 1.4 to 1.8 mm, or 1.5 to 1.7 mm. Accordingly, the inner diameters are about the same size as the width of the nozzle, +/−20%.

The interior roof surface 15f may also comprise a fin (not shown) projecting in the proximal direction and positioned centrally in a flow direction towards the nozzle outlet 15c. The fin, or a plurality of them, may be added to better control fluid distribution and ensure the fluids are evenly distributed on both sides of the fin(s).

The nozzle may, in other embodiments, comprise a nozzle floor positioned opposed to the interior roof surface in the distal direction where the nozzle floor may form part of a distal front surface of the front wall 11. A surface of such a nozzle floor may face outwardly in the distal direction and/or in a front direction of the tip part 2.

In the embodiment shown in the drawings, the nozzle does not comprise such a nozzle floor. Instead, as described, the nozzle inlets 15a, 15b are positioned proximally of the nozzle roof 15d. This makes it more convenient to mold the nozzle 15 in one piece with the front wall 11.

Figure 6A:
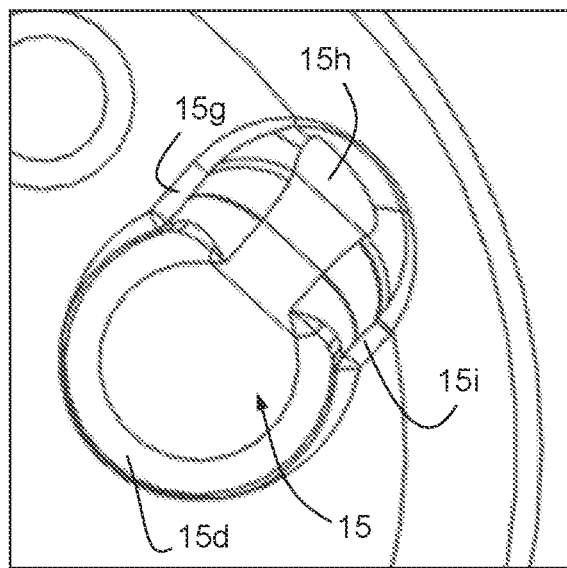
FIG. 6a shows an enlarged portion of a front view of the tip part of FIG. 2a shown in FIG. 6b.

As seen in FIGS. 5b and 6a, the nozzle 15 has three lateral side walls 15g, 15h, 15i, extending between and connecting the nozzle roof 15d with the front wall 11 of the tip part 2. Side walls 15g, 15i are lateral side walls that define the width of the nozzle outlet 15c, and side wall 15h is a back side wall positioned opposed to the nozzle outlet 15c and includes a transitional section providing a bent or inclined transition from the distal front surface of the tip part 2 to a rear end of the nozzle roof 15d, see e.g. FIG. 5. An interior surface of this back side wall 15h is rounded and forms a curvature in a transition of a fluid flow from the fluid channel(s) to the flow ejected from the nozzle outlet 15c towards the camera window 18. Two lateral interior side surfaces of the associated lateral nozzle side walls 15g, 15i are provided on each side of said back surface and are, as mentioned, arranged to form an ejected flow formed as a hand fan or a Japanese fan, see FIG. 6. A flow path of fluid flow inside the nozzle 15 towards the nozzle outlet 15c expands laterally to these lateral interior side surfaces. Accordingly, a fluid jet ejected from the nozzle outlet 15c is relatively flat in the depth direction PD and expands towards the camera window 18, shaped as a hand fan or a Japanese fan when the fluid is ejected. Hereby, the flow path extends to cover the camera window 18, preferably the entire front surface of the camera window 18, and the light windows 19. The flow velocity of fluid flow decreases towards the nozzle outlet 15c.

Figure 6B:
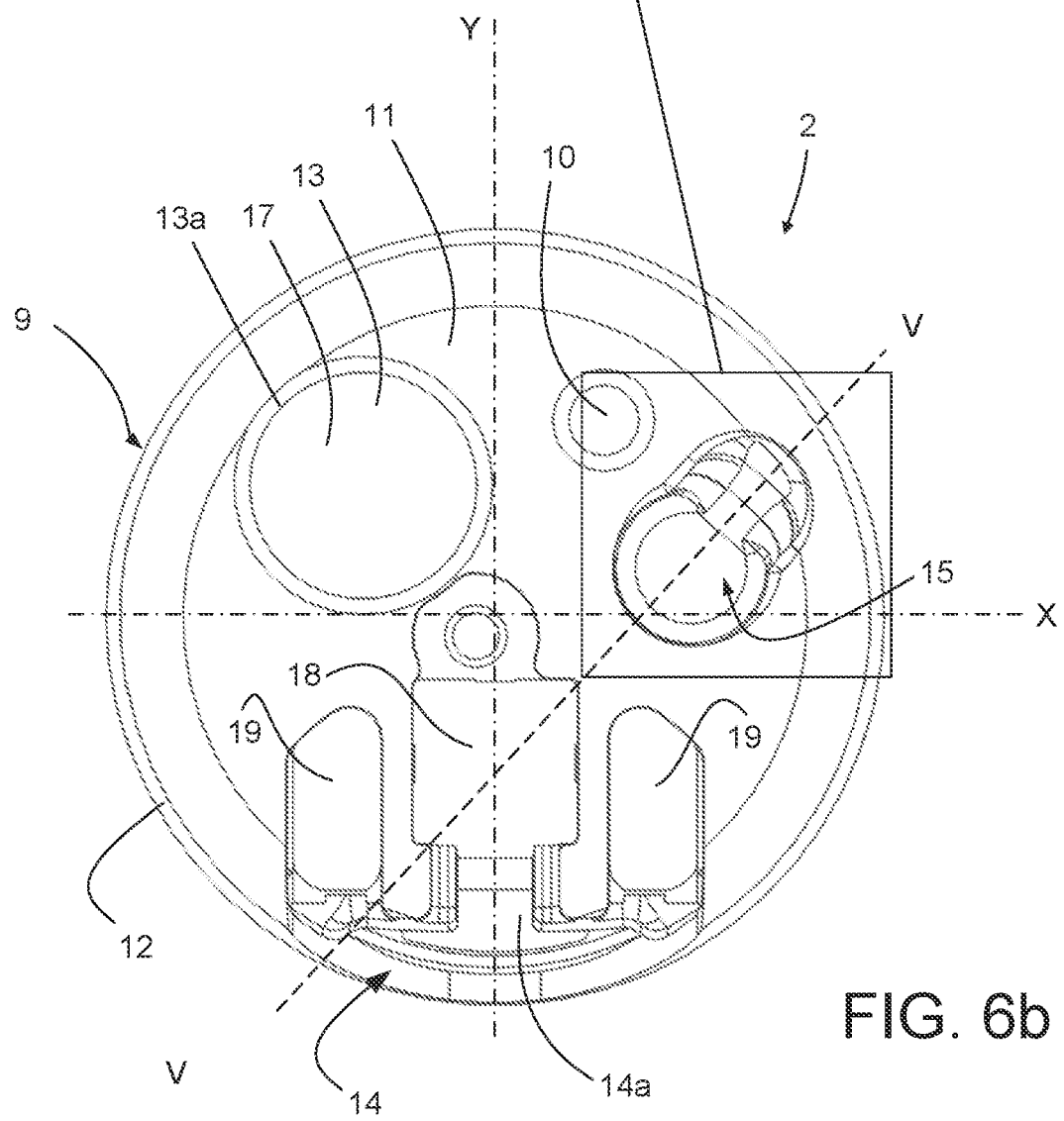

Referring to FIG. 6b, axis X and Y are shown. Axis X and Y are orthogonal and are drawn on a plane passing through the front surface of the window component 14. Axis X and Y intersect at the centerline of the distal tip. Axis Y bisects the camera window 18. A line V-V is shown which is a projection of a plane traversing and bisecting the nozzle 15. The two light windows 19 are positioned one on each side of the camera window 18, symmetrically with respect to and with an equal distance to the Y axis. As shown, the line V passes approximately through the center of the camera window 18. The side walls 15g and 15i define the width of a narrow end of a plume of fluid that is used to clean the camera window 18. The side walls 15g and 15i can be angled and separated enough to create a plume that covers the majority (at least 50%) of the light source windows 19.

The gas inlet 15b to the nozzle 15 is positioned closer to the camera window 18 than the liquid inlet 15a to the nozzle 15. The nozzle 15 inlets are positioned next to each other along the straight line V-V in a cross-sectional direction of the tip part 2, and the nozzle outlet 15c is also positioned along this line V-V. The nozzle 15 gas inlet 15b is positioned between the nozzle liquid inlet 15a and the nozzle outlet 15c. Hereby, the liquid flow path intersects the gas flow path within the nozzle 15. The camera window 18 is also positioned along this line V-V, allowing fluid to be sprayed from the nozzle outlet 15c directly towards the camera window 18. A fluid jet ejected from the nozzle 15 can directly reach both the camera window 18 and the light windows 19.

The nozzle outlet 15c faces and provides a flow path from the outlet 15c along a cross-sectional direction of the tip part 2. This allows the flow from the nozzle outlet 15c to reach the camera window part 18.

The distal front surface of the tip part 2 includes the camera window 18, the two fluid inlets from the tubes 21, 22 extending into the nozzle 15, and the working channel opening 17, wherein the camera window 18, the two fluid inlets, and the working channel opening 17 are equally distributed on the distal front surface in a circumferential direction of the tip part 2.

Flow simulations based on the design of the tip part 2 as described in connection with the drawings have shown that the tip part 2 provides an advantageous ejection of a liquid jet from the nozzle through the nozzle outlet opening. The liquid jet has at suitable fluid flow speeds a relatively small depth and a hand fan shape as described above. Only little turbulence was observed in the results of the simulations both within and outside the nozzle 15.

Figures 7A, 7B:
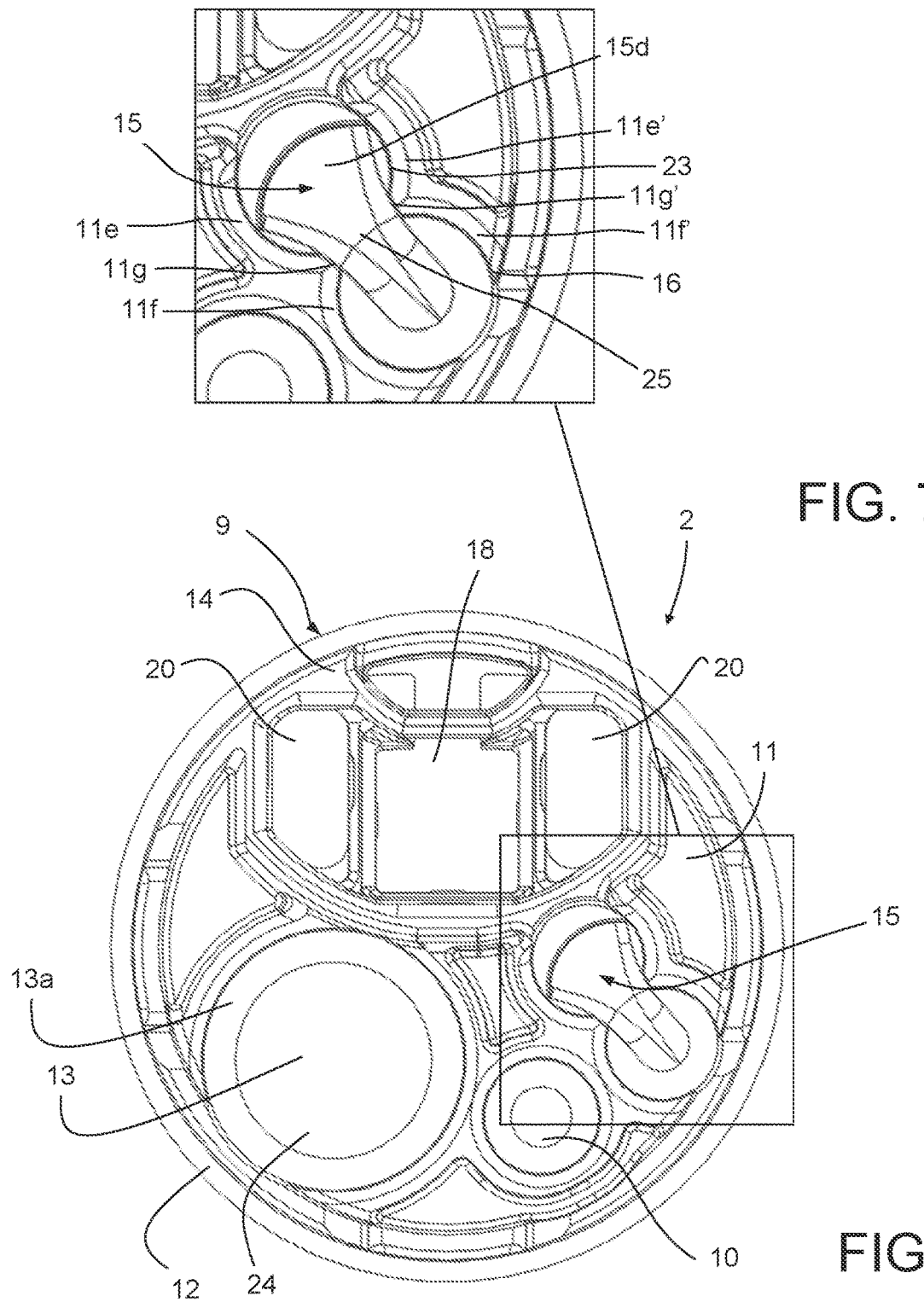

Referring to FIGS. 7a and 7b, the window component 14 includes the camera window 18 positioned in front of the vision sensor positioned within the tip part 2 and two light windows 19 extending to be positioned in front of two light sources 32 (shown in FIGS. 8a and 8b), e.g. light emitting diodes (LEDs), which are positioned within the tip part 2, see e.g. FIG. 6b. The light windows 19 are for distribution of light from the LEDs positioned within the spacing of the exterior housing 9. The camera window 18 and the light windows 19 are integrally molded in one piece with each other. As shown, the light windows 19 each includes a light guide 20 (best seen in FIG. 8b), which each extends proximally from the distal font surface of the light windows 19 towards each of the two LEDs. One LED is positioned at a proximal end of each light guide 20. The camera window 18 and the light windows 19, including the light guides 20, are integrally molded in one piece with each other from the said second polymer material. The light guides 20 are transparent and convey and control light from the LEDs. Examples and additional details pertaining to the light guides and the window component are disclosed in commonly-owned U.S. patent application Ser. No. 16/351,632, titled "A TIP PART FOR A VISION DEVICE", filed on Mar. 13, 201, which is incorporated by reference herein in its entirety.

The tip part 2 also comprises a working tube 13a positioned in the working channel 13. The exterior housing 9 accommodates part of the working tube 13a which further extends distally to the handle 5. The working tube 13a is sealed in relation to the exterior housing so that fluid in the working tube 13a will not ingress into the other interior spacing parts of the exterior housing 9. The working tube 13a includes the working outlet opening 17, which is positioned in the distal front surface of the tip part 2.

The nozzle 15 comprises a fluid joint formed by the side walls 15i, 15g, 15h and the nozzle roof 15d as well as outlets from the tubes 21, 22. The fluid joint forms a joint spacing coinciding with the fluid outlet 16a in which the flow paths of liquid and gas extending through the tubes 21, 22 are joined. Hereby, the liquid and gas can be mixed in the fluid joint.

The channels 16, 23 are formed by proximally extending walls 11e, 11e' and 11f, 11f' and extend side-by-side. An open slot 25 extends between them from an internal channel surface 11g to an internal channel surface 11g'. The distal ends of the tubes 21, 22 are positioned in the channels 16, 23, the tubes abutting each other in the slot 25 along the direction PD. Accordingly, and as best seen in FIG. 7b, the outlets from the two tubes 21, 22 are shaped like the number "8".

Figure 8A:
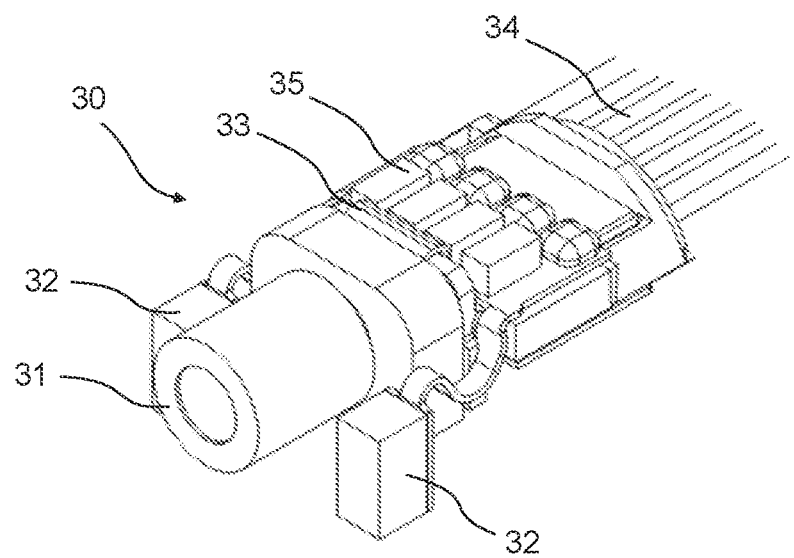
FIG. 8a is a perspective view of a camera.
Figure 8B:
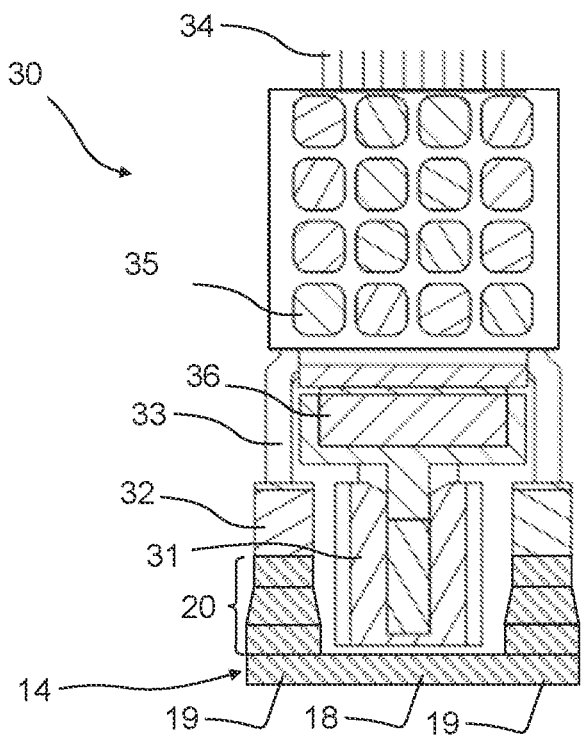

FIGS. 8a and 8b are perspective views of a conventional camera 30 including a lens barrel 31, LEDs 32, a circuit board 33 connecting the LEDs 32 to a cable 34, circuit components 35, and a vision sensor 36. The circuit board 33 may be a flexible or printed circuit board. The cable may be a flat cable which can also be part of the circuit board 33. The circuit components include passive components provided to regulate voltages for the LEDs 32 or vision sensor 36. The camera barrel 31 is opaque to block any light from reaching the vision sensor 36 except through a distal end of the camera barrel 31. The camera barrel 31 may have one or more lenses therein between the distal end and the vision sensor 36. The lenses are arranged in the lens casing or lens barrel 31 positioned between the vision sensor and the camera window 18 so that an optical axis of the lenses align and coincide with an optical axis of the vision sensor. The lenses are spaced apart by spacers. The exterior housing 9 accommodates part of the PCB.

The tip part 2 is manufactured by an embodiment of the methods according to this disclosure as described in the following.

First, the front wall 11, the circumferential wall 12, the window component 14, and the nozzle 15 are molded in one piece with each other by means of injection molding in a two-component molding process. A suitable molding tool is provided, and the first polymer material in melted or molten form is introduced into the molding tool. The second polymer material on a melted form is then introduced into the molding tool. The first and second materials are then allowed to set and form an integral component in one unit or one piece. This one piece is then removed or extracted from the molding tool. The molding tool comprises a first cavity, a second cavity, and a core. The first material is allowed to set or partly set before the second material is introduced. As mentioned, the second material is transparent, and it is introduced under higher pressure than the first material. The second material forms the window component 14, which constitutes only a minor part of the total material of the exterior housing 9. The first material is opaque at least in its set form.

Hereby, the exterior housing 9 including the nozzle 15 and the window component 14 can be manufactured automatically in one single working procedure or working step by means of the two-component injection molding process as described, which saves time and costs in manufacture of the tip part.

Then, the tubes 21, 22, 13a can easily be positioned in the channels 16, 23, 13, and the remaining components, including the camera, are positioned into the interior spacing 24 of the exterior housing 9. The tip part is also attached to the bending section.

Additional embodiments and examples include the following:

[1] A tip part for forming a tip of a disposable insertion endoscope, the tip part comprising: an exterior housing having an open proximal end for connection to other parts of the endoscope, the housing further having a front wall, wherein a circumferential wall of the housing extends from a front end of the housing to the proximal end of the housing, the circumferential wall and the front wall enclosing an interior spacing accommodating a vision sensor able to provide an image from light received from an object to be investigated; and a camera window positioned at least partly in front of the vision sensor, the camera window being

[1] positioned in, positioned in front of, or forming part of the front wall so that light received from the object can pass through the window to the vision receptor; wherein the housing further comprises a nozzle for flushing an exterior surface of the camera window with a liquid transferred to the nozzle through a liquid conduit extending from the proximal end of the housing, through the interior spacing, and to the nozzle; and wherein the front wall and the circumferential wall are integrally formed from one polymer material and are in one piece with each other, and the front wall and the nozzle are integrally formed from said one polymer material and are in one piece with each other.

[2] A tip part according to [1], wherein the front wall and the circumferential wall are integrally molded in one piece with each other, and the front wall and the nozzle are integrally molded in one piece with each other.

[3] A tip part according to [1] or [2], wherein two fluid channels for providing fluid to the nozzle are formed integrally in one piece with the exterior housing.

[4] A tip part according to [3], wherein the nozzle comprises at least part of a fluid joint, the fluid joint joining flow paths extending through the fluid channels.

[5] A tip part according to [3] or [4], wherein at least part of the two fluid channels extend side-by-side and include an open slot extending longitudinally between them.

[6] A tip part according to any one of [3] to [5], further comprising two fluid tubes provided separately from the fluid channels, wherein one of the two fluid tubes is positioned in each of the two fluid channels.

[7] A tip part according to any one of [3] to [6], wherein a fluid outlet from each of the fluid tubes terminates at or in the nozzle so that they form fluid inlets into the nozzle.

[8] A tip part according to any one of [1] to [7], wherein a distal front surface of the tip part includes the camera window, two fluid inlets extending into the nozzle, and a working channel opening, wherein the camera window, the two fluid inlets, and the working channel window are equally distributed on the front surface in a circumferential direction of the tip part.

[9] A tip part according to any one of [1] to [8], wherein a first nozzle fluid inlet to the nozzle is positioned closer to the camera window than a second nozzle fluid inlet to the nozzle.

[10] A tip part according to any one of [1] to [9], wherein a ratio of depth:width of a nozzle outlet opening is between 1:2 and 1:12.

[11] A tip part according to any one of [1] to [10], further comprising a window part positioned at or in the front wall, wherein the window part comprises the camera window, and the window part is formed of a second polymer material, the second polymer material being different from said one polymer material.

[12] A tip part according to any one of [1] to [11], further comprising a light guide positioned in front of a light source.

[13] A method of manufacture of tip part for forming a tip of a disposable insertion endoscope, wherein the tip part comprises: an exterior housing having an open proximal end for connection to other parts of the vision device, the housing further having a front wall, wherein a circumferential wall of the housing extends from a distal end of the housing to the proximal end of the housing, the circumferential wall and the front wall enclosing an interior spacing accommodating a vision sensor able to provide an image from light received from an object to be investigated; and a camera window positioned at least partly in front of the vision sensor, the camera window being positioned in, positioned in front of, or forming part of the front wall so that light received from the object can pass through the camera window to the vision sensor; wherein the housing further comprises a nozzle for flushing an exterior surface of the camera window with a liquid transferred to the nozzle through a liquid conduit extending from the proximal end of the housing, through the interior spacing, and to the nozzle; said method comprising the step of: integrally molding the exterior housing in one piece so that the front wall and the circumferential wall are molded in one piece with each other and so that the front wall and the nozzle are integrally molded in one piece with each other.

[14] A method according to [13], further comprising the step of integrally molding the exterior housing and the camera window in one piece with each other in a multi-component molding process, in which molding process the exterior housing and the camera window are manufactured from two different materials.

[15] An endoscope comprising a tip part according to any one of [1] to and/or comprising a tip part manufactured according to any one of and [14].

LIST OF REFERENCE NUMERALS

1 Endoscope
2 Tip part
3a Distal end
3b Proximal end
4 Insertion tube
4a Outer Sheath
5 Handle
6 Control button
7 Bending section
8 Cable
8a Cable connector
9 Exterior housing
9a Open proximal end
10 Water jet outlet
11 Distal front wall
11a Distal surface
12 Circumferential wall
12b Step
13 Working tube
13a Working tube
14 Camera window
14a Exterior surface
15 Nozzle
15a Liquid inlet
15b Fluid outlet
15c Nozzle outlet
15d Nozzle roof
15e Top edge
15f Side wall
15g Side wall
15h Side wall
15i Gas inlet
16 Liquid channel
17 Working channel opening
18 Camera window part
19 Light window part
20 Light guide
21 Liquid tube
22 Gas tube
23 Gas channel
24 Interior spacing
25 Slot
30 Camera
31 Camera barrel 32 LED
33 Circuit board
34 Cable
35 Circuit component
36 Vision sensor

The invention claimed is:

1. An endoscope comprising:
a gas tube comprising a distal end;
a liquid tube comprising a distal end, the distal end of the gas tube and the distal end of the liquid tube being longitudinally contiguous; and
a tip part including:
a housing having a proximal end, a front end opposite the proximal end, a circumferential wall extending from the front end to the proximal end, a front wall, and a nozzle, a gas channel receiving the distal end of the gas tube, and a liquid channel receiving the distal end of the liquid tube, the circumferential wall and the front wall defining an interior spacing of the housing;
a vision sensor positioned in the housing; and
a camera window positioned at the front end of the housing;
wherein the nozzle comprises a nozzle roof, a nozzle outlet, and two lateral walls, the nozzle roof positioned distally of the gas channel and the liquid channel, the two lateral walls connecting the nozzle roof to the front wall and including first ends and second ends opposite the first ends, the second ends being closer to each other than the first ends, the gas channel and the liquid channel being located between the two lateral walls,
wherein a plane parallel to a longitudinal dimension of the distal tip traverses the liquid channel, the nozzle outlet and the camera window, and
wherein the nozzle roof and the two lateral walls are sized and shaped to cause a gas and a liquid discharged through the distal ends of the gas tube and the liquid tube to impinge on, and be redirected by, the nozzle roof through the nozzle outlet toward the camera window.

2. The endoscope of claim 1, wherein the front wall, the circumferential wall, the camera window, and the nozzle are integrally molded in one piece with each other, the front wall, the circumferential wall, and the nozzle comprised of a first polymer material and the window being comprised of a second polymer material different from the first polymer material.

3. The endoscope of claim 2, wherein the gas channel and the liquid channel are formed integrally in one piece with the housing.

4. The endoscope of claim 1, wherein the nozzle comprises at least part of a fluid joint, the fluid joint joining liquid and gas flow paths extending distally from the gas channel and the liquid channel to the nozzle roof.

5. The endoscope of claim 1, wherein the gas channel abuts the liquid channel and an open slot extends longitudinally between the gas channel and the liquid channel.

6. The endoscope of claim 1, wherein the gas channel is positioned between the camera window and the liquid channel and extends distally further than any part of the liquid channel.

7. The endoscope of claim 1, further comprising a handle, an insertion tube, a bending section, wherein the gas tube and the liquid tube extend from the handle to the tip part through the insertion tube and the bending section.

8. The endoscope of claim 1, further comprising a window component including the camera window and a light window, wherein the front wall comprises a cutout and the window component is sealingly bonded to the front wall at the cutout.

9. The endoscope of claim 8, wherein the window component comprises a light guide extending proximally from the light window, the light guide including a section with an increasing cross-sectional area in the distal direction.

10. The endoscope of claim 1, wherein the nozzle comprises a transition wall positioned opposite the nozzle outlet and connecting the front wall and the nozzle roof adjacent the second ends of the two lateral walls.

11. The endoscope of claim 1, wherein the nozzle outlet comprises a depth, and wherein a depth to width ratio of the nozzle outlet is between 1:5.6 and 1:12.

12. The endoscope of claim 1, wherein a gap between the first ends defines a width of the nozzle outlet.

13. An endoscope comprising:
a gas tube comprising a distal end;
a liquid tube comprising a distal end, the distal end of the gas tube and the distal end of the liquid tube being longitudinally contiguous; and
a tip part including:
a front wall;
a nozzle integrally formed in one piece with the front wall;
a vision sensor; and
a camera window sealingly bonded to the front wall and positioned distally of the vision sensor;
a gas channel and a liquid channel, the gas channel and the liquid channel extending proximally from the front wall, the gas channel receiving the distal end of the gas tube and the liquid channel receiving the distal end of the liquid tube,
wherein the nozzle comprises a nozzle roof, a nozzle outlet, and two lateral walls, the nozzle roof positioned distally of the gas channel and the liquid channel, the two lateral walls connecting the nozzle roof to the front wall and including first ends defining a width of the nozzle outlet and second ends opposite the first ends, the second ends being closer to each other than the first ends, the gas channel and the liquid channel being located between the two lateral walls,
wherein a plane parallel to a longitudinal dimension of the distal tip traverses the liquid channel, the nozzle outlet and the camera window, and
wherein the nozzle roof and the two lateral walls are sized and shaped to cause a gas and a liquid discharged through the distal ends of the gas tube and the liquid tube to impinge on, and be redirected by, the nozzle roof through the nozzle outlet toward the camera window.

14. The endoscope of claim 13, wherein the gas channel and the liquid channel are formed integrally in one piece with the front wall.

15. The endoscope of claim 14, wherein the nozzle comprises at least part of a fluid joint, the fluid joint joining liquid and gas flow paths extending distally from the gas channel and the liquid channel to the nozzle roof.

16. The endoscope of claim 13, further comprising a light guide including a section with an increasing cross-sectional area in the distal direction.

17. The endoscope of claim 13, wherein the nozzle outlet comprises a depth, and wherein a depth to width ratio of the nozzle outlet is between 1:5.6 and 1:12.

18. A method to manufacture an endoscope comprising a tip part, the method comprising:

integrally molding in one piece a front wall, a circumferential wall, and a nozzle, the front wall and the circumferential wall forming a housing defining an internal space, the front wall including a gas channel and a liquid channel;

inserting a distal end of a gas tube into the gas channel;

inserting a distal end of a liquid tube into the liquid channel, at least after insertion the distal end of the liquid tube and the distal end of the gas tube being contiguous;

positioning a vision sensor in the internal space;

positioning a camera window at the front end of the housing;

wherein the nozzle comprises a nozzle roof, a nozzle outlet, and two lateral walls, the nozzle roof positioned distally of the gas channel and the liquid channel, the two lateral walls connecting the nozzle roof to the front wall and including first ends defining a width of the nozzle outlet and second ends opposite the first ends, the second ends being closer to each other than the first ends, the gas channel and the liquid channel being located between the two lateral walls, wherein a plane parallel to a longitudinal dimension of the distal tip traverses the liquid channel, the nozzle outlet and the camera window, and wherein the nozzle roof and the two lateral walls are sized and shaped to cause a gas and a liquid discharged through the distal ends of the gas tube and the liquid tube to impinge on, and be redirected by, the nozzle roof through the nozzle outlet toward the camera window.

19. The method of claim 18, further comprising integrally molding the housing and the camera window in one piece with each other, wherein the housing and the camera window comprise different materials.

20. The method of claim 19, further comprising integrally molding a light guide with the camera window in one piece with each other.

21. The method of claim 18, wherein the gas channel is positioned between the camera window and the liquid channel and extends distally further than any part of the liquid channel.

\* \* \* \* \*